United States Patent
Doherty et al.

(10) Patent No.: US 6,316,614 B1
(45) Date of Patent: *Nov. 13, 2001

(54) GENETIC CONTROL OF ACETYLATION AND PYRUVYLATION OF XANTHAN BASED POLYSACCHARIDE POLYMERS

(75) Inventors: Daniel H. Doherty; Donna M. Ferber, both of Boulder, CO (US); John D. Marrelli, Houston, TX (US); Rebecca W. Vanderslice, Boulder; Randal A. Hassler, Lafayette, both of CO (US)

(73) Assignee: CP Kelco U.S., Inc., Wilmington, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 08/475,823

(22) Filed: Jun. 7, 1995

Related U.S. Application Data

(62) Division of application No. 08/232,416, filed on Apr. 25, 1994, now Pat. No. 5,514,791, which is a continuation of application No. 07/696,732, filed on May 7, 1991, which is a continuation-in-part of application No. 07/566,875, filed on Aug. 13, 1990, now abandoned, which is a continuation-in-part of application No. 07/384,621, filed on Jul. 25, 1989, now abandoned, which is a continuation of application No. 07/029,090, filed on Mar. 23, 1987, now abandoned, which is a continuation-in-part of application No. 06/844,435, filed on Mar. 26, 1986, now abandoned, which is a continuation-in-part of application No. 06/762,878, filed on Aug. 6, 1985, now Pat. No. 4,713,449.

(51) Int. Cl.[7] .............................. C08B 37/00; C07H 1/00; C07H 13/02; C12P 19/06

(52) U.S. Cl. .................... 536/114; 536/115; 536/119; 536/123; 435/104

(58) Field of Search .................... 536/114, 115, 536/119, 123; 435/104

(56) References Cited

U.S. PATENT DOCUMENTS

| | | | |
|---|---|---|---|
| 3,000,790 | 9/1961 | Jeanes et al. | 536/1.1 |
| 3,054,689 | * 9/1962 | Jeanes et al. | 536/123 |
| 3,096,293 | 7/1963 | Jeanes et al. | 435/104 |

(List continued on next page.)

FOREIGN PATENT DOCUMENTS

| | | |
|---|---|---|
| 744365 | * 10/1966 | (CA) . |
| 066961 | 12/1982 | (EP) . |
| WOA8705938 | 10/1987 | (WO) . |
| WOA8705939 | 10/1987 | (WO) . |

OTHER PUBLICATIONS

Bradshaw, et al., Modified Xanthan—Its Preparation Carbohydrate Polymers, 3:23–38 (1983).
Dentini et al., "Conformational properties of Xanthan Derivatives in Dilute Aqueous Solution," Int. J. Biol. Macromol 6:93–98 (Apr. 1984).

(List continued on next page.)

Primary Examiner—Gary Geist
Assistant Examiner—Everett White
(74) Attorney, Agent, or Firm—Fitzpatrick, Cella, Harper & Scinto

(57) ABSTRACT

Variant xanthan gums are provided which include a water-soluble polysaccharide polymer comprising repeating pentamer units having a D-glucose:D-mannose:D-glucuronic acid ratio of about 2:2:1, and a water-soluble polysaccharide polymer comprising repeating tetramer units having a D-glucose:D-mannose:D-glucuronic acid ratio of about 2:1:1. The D-glucose moieties are linked in a beta-[1,4] configuration. The inner D-mannose moieties are linked in an alpha-[1,3] configuration, generally to alternate glucose moieties. The D-glucuronic acid moieties are linked in a beta-[1,2] configuration to the inner mannose moieties. The outer mannose moieties are linked to the glucuronic acid moieties in a beta-[1,4] configuration. Processes for preparing the polysaccharide polymers are also provided.

42 Claims, 13 Drawing Sheets

U.S. PATENT DOCUMENTS

| | | | |
|---|---|---|---|
| 3,433,708 | 3/1969 | McNeely | 435/104 |
| 4,051,317 | 9/1977 | Towle | 536/114 |
| 4,182,860 | 1/1980 | Naslund et al. | 536/114 |
| 4,214,912 | 7/1980 | Racciato et al. | 536/114 |
| 4,245,046 | 1/1981 | Demain et al. | 435/104 |
| 4,260,741 | 4/1981 | Schuppner | 536/114 |
| 4,296,203 | 10/1981 | Wernau | 435/104 |
| 4,329,448 | 5/1982 | Cox et al. | 536/114 |
| 4,352,741 | 10/1982 | Wernau | 252/8.554 |
| 4,357,423 | 11/1982 | Cox et al. | 435/101 |
| 4,394,447 | 7/1983 | Cadmus et al. | 435/104 |
| 4,407,951 | 10/1983 | Weisrock et al. | 435/104 |
| 4,713,449 | 12/1987 | Vanderslice et al. | 536/123 |
| 4,868,293 | 9/1989 | Vanderslice et al. | 536/123 |
| 5,514,791 * | 5/1996 | Doherty et al. | 536/114 |
| 5,559,015 | 9/1996 | Capage et al. | 435/104 |
| 5,948,651 * | 7/1999 | Doherty et al. | 435/101 |

OTHER PUBLICATIONS

Ditta, et al., "Plasmids Related to the Broad Host Range Expression," pRK290, Useful for Gene Cloning and for Monitoring Gene Expression Plasmid 13: 149–153 (1985).

EPO Search Report of EPO Application No. 90113985.7 dated Feb. 27, 1992.

Holzwarth et al. "Pyruvate–Free Xanthan," Carbohydrate Research 76:277–280 (1979).

Gay, et al., "Cloning Structural Gene sacB, Which Codes for Endenzyme Lavansucrase of Bacillus Subtilis: Expression of the Gene Escherichia Coli," Journal of Bacteriology, 153:1424–1431 (1983).

Ielpi, et al., "Xanthan gum Biosynthesis Acetyzation Occurs at the Prenyl–Phospho–Sugan Stage," Biochem. Intern., 6(3):323–333 (1983).

Jansen et al., Carbohydrate Research, 45:275–282 (1975).

Joyce et al., Nucleotide Sequence of the Escherichia Coli pol A Gene and Primary Structure of DNA Polymerase I, J. Biol. Chem. 257:(4) 1958–1964, 1982.

Okita et al., "Biosynthesis of Bacterial Glycogen," J. Biol. Chem. 256:(13) 6944–6952, 1981.

Orentasi et al., "Pyruvic Acid Content and Constituent Sugars of Exocellular Polysaccharides From Different Species of the Genus Xanthomonas," Can. J. Microbiol., 9:427–430 (1963).

Philips et al., "A High–Pyruvate Xanthan for EOR," Soc. Pet 25(4):594–602 (1985).

Rinaudo, et al., "$^1$H and $^{13}$C NMR Investigation of Xanthan Gum," Macromolecules, 16(5):816–819 (1983).

Siddiqui, Carbohydrate Research, 4:284–291 (1967).

Slonecker et al., Canadian Journal of Chemistry, 40:2066–2071 (1962).

Slonecker et al., Canadian Journal of Chemistry, 42:1261–1269 (1964).

Smith, et al., "Influence of the Pyruvate Content of Xanthan on Macromolecular Association in Solution," (1980).

Sutherland, "Xanthomonas Polysaccharides–Improved Methods For Their Comparison," Carbohydrate Polymers, 1(2):107–115 (1981).

Tako, et al., "Rheological Properties of Deacetylated Xanthan In Aqueous Media," Agric. Biol. Chem., 48:2987–2993 (1984).

Holzwarth et al. "Pyvuvate–Free Xanthan" Carbohydrate Research 76:277–280 (1979).*

Dentini et al, "Conformation Properties of Xanthan Derivatives in Dilute Aqueous Solution," Int. J. Biol. Macromol 6:93–98 (Apr. 1984).*

Kirchev et al., 'Biosynthesis of Xanthan by Xanthomonas Campestris', Biotekhnol. Biotekh. (1987), (6), 27–31.*

* cited by examiner

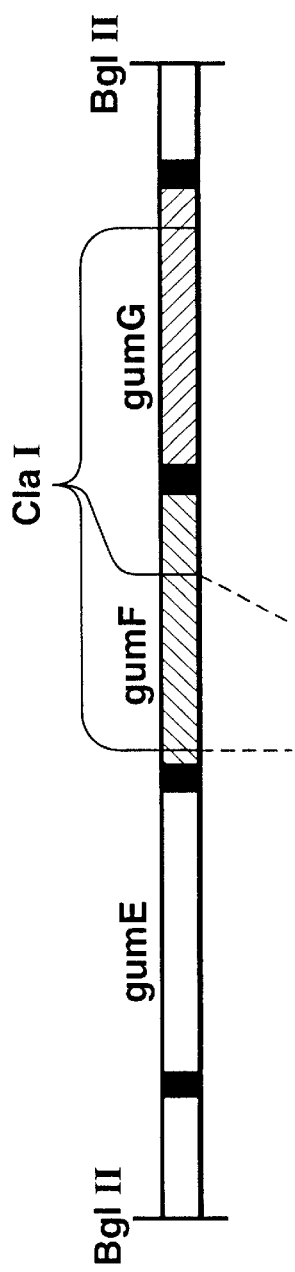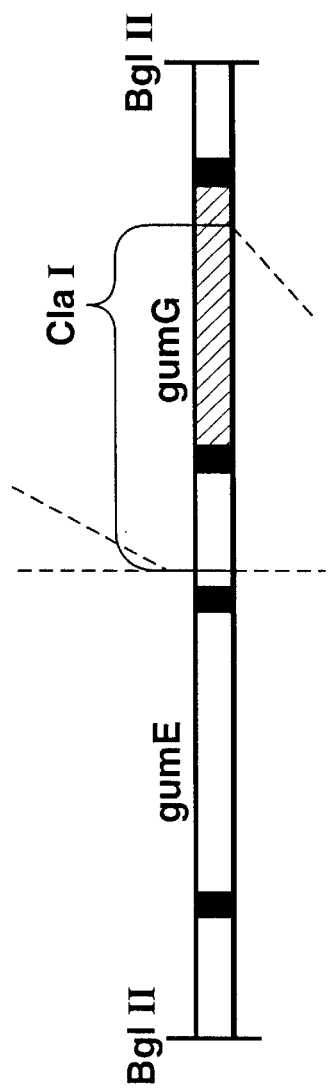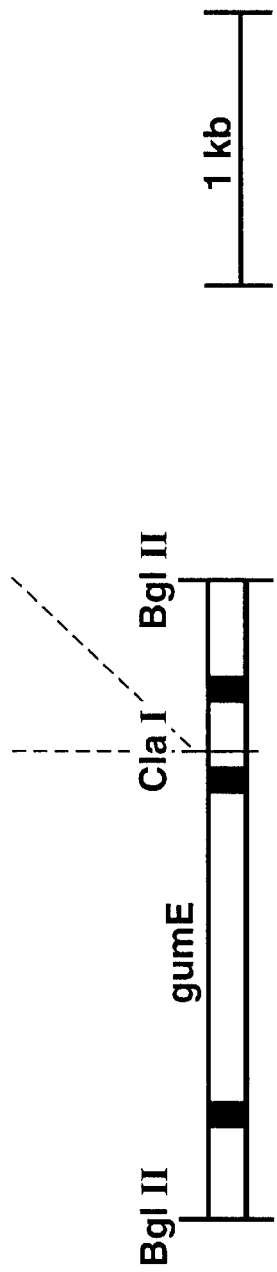
FIG. 7a
pSlBgl
FIG. 7b
pSlBgl
ΔCla
FIG. 7c
pSlBgl
ΔCla2

GENETIC CONTROL OF ACETYLATION AND PYRUVYLATION OF XANTHAN BASED POLYSACCHARIDE POLYMERS

This application is a divisional of application Ser. No. 08/232,416, filed Apr. 25, 1994 (U.S. Pat. No. 5,514,791), which is a continuation of application Ser. No. 07/696,732, filed May 7, 1991, which is a continuation-in-part of application Ser. No. 07/384,621, filed Jul. 25, 1989 (abandoned). This application is also a continuation-in-part of application Ser. No. 07/566,875, filed Aug. 13, 1990 (abandoned), which is a continuation of application Ser. No. 07/029,090, filed March 23, 1987 (abandoned), which is a continuation-in-part of application Ser. No. 06/844,435, filed Mar. 26, 1986 (abandoned), which is a continuation-in-part of application Ser. No. 06/762,878, filed Aug. 6, 1985 (U.S. Pat. No. 4,713,449).

BACKGROUND OF THE INVENTION

This invention relates to polysaccharide polymers. In particular, it relates to xanthan-based polysaccharide polymers, defined herein as polymers structurally similar to xanthan gum and produced by components of the xanthan biosynthetic pathway, including those xanthan-based polymers modified so that the outer mannose can be specifically acetylated but not pyruvylated, pyruvylated but not acetylated, or unmodified while the inner mannose can be independently controlled to be acetylated or unmodified.

Xanthan gum is produced by bacteria of the genus Xanthomonas, in particular by microorganisms of the species *X. campestris*. Xanthan gum is a widely used product due to its unusual physical properties, i.e., its extremely high specific viscosity and its pseudoplasticity. It is commonly used in foods as a thickening agent and in secondary or tertiary oil recovery as a mobility control and profile modification agent, as well as in petroleum drilling fluids.

Chemically, xanthan gum is an anionic heteropolysaccharide. The repeating unit of the polymer is a pentamer composed of five sugar moieties, specifically two glucose, one glucuronic acid and two mannose moieties. These sugar residues are arranged such that the glucose moieties form the backbone of the polymer chain, with side chains of mannose-glucuronic acid-mannose residues generally extending from alternate glucose moieties. Usually, this basic structure is specifically acetylated and pyruvylated, as described, for example, by Janson, P. E., Kenne, L., and Lindberg, B., in Carbohydrate Research, 45:275–282 (1975) and Melton, L. D., Minot, L., Rees, D. A., and Sanderson, G. R., in Carbohydrate Research, 46:245–257 (1976), each of which is specifically incorporated herein by reference. The extent of acetylation and pyruvylation is known to vary. The structure of xanthan gum is depicted in formula I below:

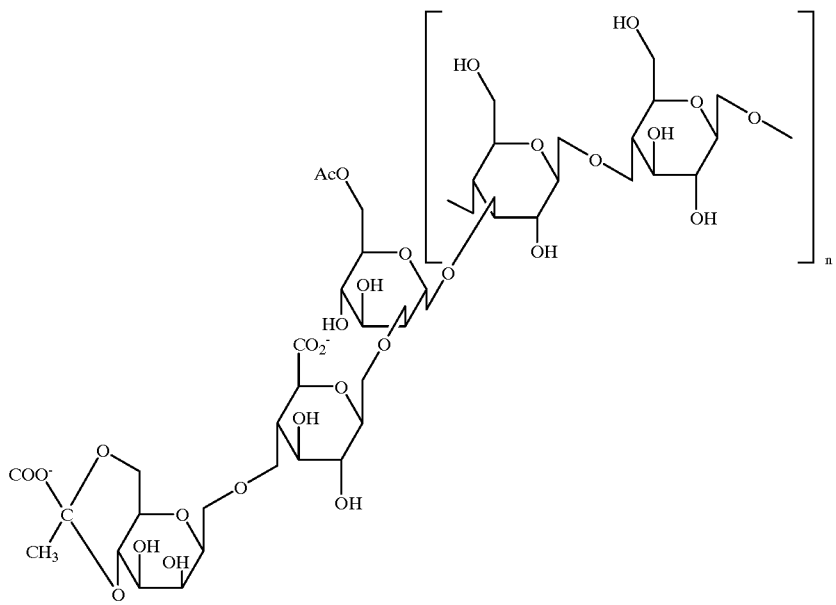

In spite of the broad utility of naturally-occurring xanthan gum, there are some situations where its physical properties become limiting. In particular, in secondary or tertiary oil recovery it is not uncommon for the temperature of the oil bearing reservoir and the salt concentrations in the reservoir brine to be higher than are optimal for xanthan solutions. When these conditions occur, xanthan can precipitate, flocculate and/or lose its viscosity. Therefore, new viscosifying products which perform well at various conditions encountered during oil recovery, such as high temperature and high salt concentrations would be desirable.

The present invention discloses a family of xanthan-based polysaccharides having improved properties relative to naturally-occurring xanthan gum. Modifications of xanthan gum have been previously described. For example, Bradshaw et al. (Carbohydrate Polymers, 3:23–38 (1983)) describe methods for preparing chemically-modified xanthan gum which is deacetylated or depyruvylated. Various means of chemically deacetylating xanthan gum produced by *Xanthomonas campestris* also are described in U.S. Pat. Nos. 3,000,790 and 3,054,689. To date, the predominant method utilized for these deacetylation processes has been chemical removal of the acetate moieties from normally acetylated xanthan gum. It has been found that chemical processes for deacetylating xanthan gums can result in a number of undesirable side effects and may cause hydrolysis of the glycosidic backbone, resulting in an irreversible change in the conformation of the molecule and lowered molecular weight.

Some of the Theological properties of deacetylated xanthan in aqueous media are known. See, e.g., Tako and Nakamura, Agric. Biol. Chem. 48:2987–2993 (1984) and U.S. Pat. Nos. 3,000,790 and 3,054,689. Also, a method of increasing the viscosity of an aqueous solution using a deacetylated polysaccharide is described in U.S. Pat. No. 3,096,293. Thus, a method for obtaining non-acetylated xanthan which does not cause untoward side effects has been sought.

Xanthan gum can be chemically depyruvylated as well, as described by Holzwarth and Ogletree in Carbo. Res. 76:277–280 (1979). This chemical method of depyruvylation also can alter the xanthan polymeric unit and/or cause hydrolysis of the glycosidic backbone. While a strain of X. campestris has been described in U.S. Pat. No. 4,296,203 which produces non-pyruvylated xanthan gum, this non-pyruvylated gum was either fully acetylated or deacetylated using chemical means.

Additionally, the extent of acetylation of the internal mannose on the xanthan side chain and the extent of the pyruvylation of the terminal mannose may vary. The present inventors believe that a fully acetylated and/or fully pyruvylated xanthan will have improved Theological properties for certain oil recovery purposes.

Moreover, the present inventors have identified polysaccharides which are based on alterations of the normal xanthan pentamer building block. These polymers exhibit improved rheological properties over normal xanthan gum with respect to shear rate, their ability to tolerate salinity and their response to temperature as it affects their viscosifying properties. These altered polysaccharides include the polytrimer which is depicted below and the non-acetylated polytetramer.

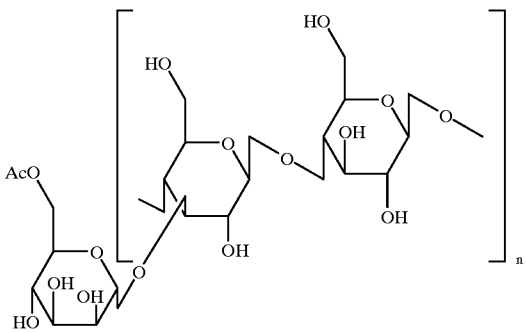

These polysaccharides also include the acetylated and non-acetylated polytrimer described by Vanderslice et al in copending U.S. patent application Ser. No. 762,878, entitled "A Polysaccharide Polymer Made By Xanthomonas," filed Aug. 6, 1985, which is specifically incorporated herein by 1 reference.

An object of the present invention is to provide a family of polysaccharide polymers which are better viscosifiers of water than naturally-occurring xanthan gum. Another object of the present invention is to provide a family of polysaccharide polymers having improved Theological properties over naturally-occurring xanthan gum at elevated temperatures and/or in the presence of salts and which members possess other desired properties.

An object of the present invention is to provide a family of polysaccharide xanthan polymers in which the inner mannose is acetylated or unmodified while the outer mannose is acetylated, pyruvylated or unmodified.

It is also an object of the present invention to provide an in vitro method for obtaining these products and microorganisms having the ability to produce members of this family of polysaccharide polymers in vivo. A further object of the present invention is to provide processes for preparing members of this family of polysaccharides by aerobically fermenting microorganisms having the ability to produce the various polysaccharide polymers.

It is also an object of the present invention to provide a process for preparing members of this family of polysaccharides by aerobically fermenting microorganisms containing chromosomal mutations which give these microorganisms the ability to produce the various polysaccharide polymers.

Additional objects and advantages of the invention will be set forth in part in the description which follows, and in part will be obvious from the description, or may be learned by practice of the invention. The objects and advantages may be realized and attained by means of the instrumentalities and combinations particularly pointed out in the appended claims.

SUMMARY OF THE INVENTION

To achieve the objects and in accordance with the purposes c. the invention, as embodied and broadly described herein, there is provided a composition comprising a polysaccharide polymer having la D-glucose: D-mannose: D-glucuronic acid ratio of about 2:2:1, wherein the D-glucose moieties are linked in a beta-[1,4] configuration, inner D-mannose moieties are linked in an alpha-[1,3] configuration, generally to alternate glucose moieties, the D-glucuronate moieties are linked in a beta-[1,2] configuration to the inner mannose moieties and outer mannose moieties are linked to the D-glucuronate moieties in a beta-[1,4] configuration.

To further achieve the objects and in accordance with the purposes of the present invention, there is provided a composition comprising xanthan gum wherein the inner mannose moieties are acetylated at the 6-0 position. Another structure contemplates both the inner and outer mannose moieties being acetylated. A further structure is provided having a portion of the outer mannose moieties pyruvylated at the 4-6 position and a portion acetylated. Another structure is provided with the outer mannose moieties pyruvylated at the 4-6 position and the inner mannose moieties acetylated at the 6-0 position. Two additional structures are provided, one having the outer mannose moieties pyruvylated at the 4-6 position and the other having the outer mannose moieties acetylated.

To further achieve the objects and in accordance with the purposes of the invention, as embodied and broadly described herein, there is provided a composition comprising a polysaccharide polymer having a D-glucose: D-mannose: D-glucuronic acid ratio of about 2:1:1, wherein the D-glucose moieties are linked in a beta-[1,4] configuration, the D-mannose moieties are linked in an alpha-[1,3] configuration, generally to alternate glucose moieties, and the D-glucuronate moieties are linked in a beta-[1,2] configuration to the mannose moieties. This polysaccharide polymer is herein termed "polytetramer" because it consists of a repeating tetramer unit: glucose-glucose-mannose-glucuronic acid. There is also provided a polytetramer composition, as described above, wherein at least 90%, preferably 95% and most preferably 100% of the mannose moieties are acetylated at the 6-0 position as well as a polytetramer which is non-acetylated.

Also, the present invention relates to a xanthan gum herein referred to as "fully acetylated xanthan gum," wherein at least 190% of the internal mannose moieties are acetylated, preferably 95% and more preferably 100%, are acetylated. Also, the present invention relates to a xanthan gum wherein at least 90% of the terminal mannose moieties, preferably 95% and more preferably 100%, are pyruvylated, herein referred to as "fully-pyruvylated xanthan gum."

This invention also contemplates processes for the production of the polysaccharide polymers described above. The polysaccharide polymers of this invention can be made generally by genetic manipulations of the microbial biosynthetic pathways which lead to the production of polysaccharides. In particular, microbial pathways for the production of xanthan gum may be manipulated to create an in vivo or in vitro system for the production of an altered polymeric unit. Thus, systems can be created through the use of mutated Acetylase I, Acetylase II and Ketalase genes, in particular, to create polysaccharides which are acetylated or pyruvylated to varying degrees. For example, it is contemplated that xanthan gum which is 10%, 20%, 30%, 40%, or 50% can be synthesized as well as xanthan which is 10%, 20%, 30%, 40%, 50%, 60%, 70%, or 80% pyruvylated. Microorganisms which produce the present polysaccharide polymers in vivo and methods of using these polysaccharide polymers are also disclosed.

The inventors also describe an in vivo system for the production of an altered polymeric unit where the mutated genes are incorporated into the chromosome of the microorganism rather than in a recombinant plasmid. This chromosomal deletion mutation is advantageous because it eliminates potential problems with plasmid maintenance, and also could contribute to strain stability.

It is understood that both the foregoing general description and the following detailed description are exemplary and explanatory only and are not restrictive of the invention, as claimed. The accompanying drawings, which are incorporated in and constitute a part of this specification, illustrate various embodiments of the invention and, together with the description, serve to explain the principles of the invention.

BRIEF DESCRIPTION OF THE DRAWINGS

FIG. 7a shows a map of a 4.3 Kb BglII fragment of the gum gene cluster that contains the gum F and gum G genes.

FIG. 7b shows the deletion mutation of the Cla I fragment internal to the gum F gene.

FIG. 7c shows deletion of the second Cla I fragment which Recreates an in-frame fusion of the proximal portion of the gum F gene with the distal portion of the gum G gene.

DETAILED DESCRIPTION OF THE INVENTION

Reference will now be made in detail to the presently preferred embodiments of the present invention which, together with the following examples, serve to explain the principles of the invention. All references referred to herein are hereby specifically incorporated herein by reference.

The polysaccharide polymers of the present invention have been described in detail above. These polysaccharide polymers can be produced in vitro with a cell-free enzyme system or can be produced in vivo by growing cells of an appropriate mutant strain. Other means of preparing the polysaccharide polymers are also described below.

In Vitro Polysaccharide Synthesis

The basic method relating to the use of a cell-free system to make non-variant xanthan gum is described by Ielpi, L., Couso, R. O., and Dankert, M. A. in FEBS Letters 130:253–256 (1981), specifically incorporated herein by reference. It has been found that a modified version of this method may be employed to create the variant polysaccharides of this invention.

For this novel, modified method, the in vitro cell-free system is prepared generally by lysing cells of a microorganism of the genus Xanthomonas, preferably *Xanthomonas campestris*, in the presence of a suitable buffer, preferably including EDTA, and obtaining the appropriate biosynthetic enzymes which are able to subsequently process exogenously added substrates. This general method for this in vitro system in described in U.S. Pat. No. 4,713,449 of Vanderslice et al., specifically incorporated herein by reference. Alternate means of lysis may be used, including but not limited to sonication, French Pressure cell, detergent treatment, enzyme treatment and combinations thereof.

Generally, to produce the variant polysaccharides of the present invention, a lysate of a microorganism possessing the enzymes required to assemble the desired polysaccharide is incubated with the appropriate substrates, which, depending on the gum desired, may include UDP-glucose, GDP-mannose, UDP-glucuronic acid, acetyl-CoA and phosphoenolpyruvate. The choice of substrates is dependent on the polysaccharide which it is desired to produce. For example, a non-acetylated polysaccharide is obtained-by eliminating acetyl-CoA as a substrate. Similarly, a non-pyruvylated gum is obtained by eliminating phosphoenolpyruvate as a substrate. Chemical and/or enzymatic treatment of the cell lysates in order to deplete endogeneous substrates will be evident to one skilled in the art.

Figure 12:
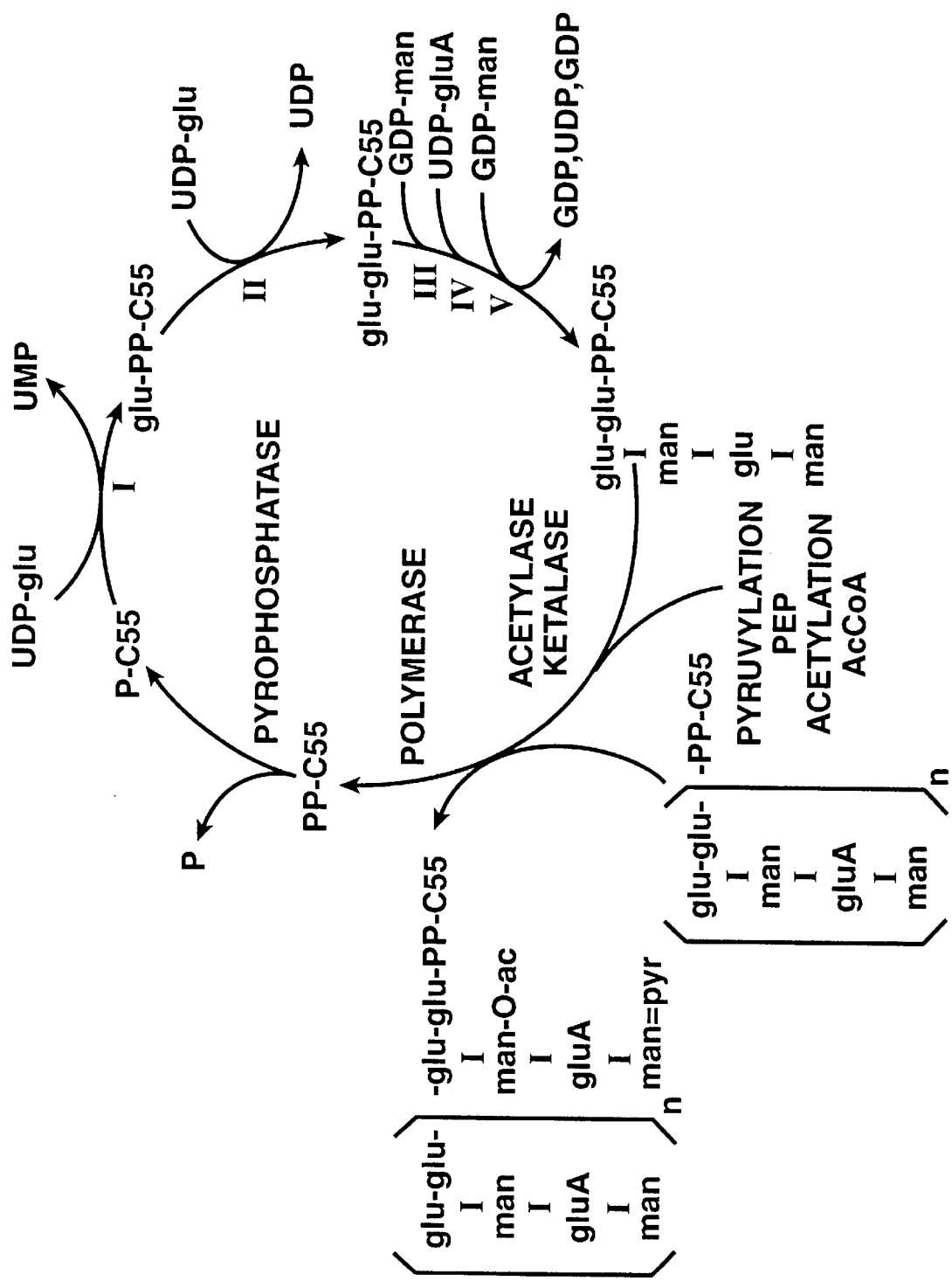
FIG. 12 depicts the presumed pathway of xanthan gum biosynthesis. Abbreviations used are: Glu=Glucose; GluA= Glucuronic acid; Man-Mannose; Glu-Glu=Cellobiose; P=Phosphate; PP=Pyrophosphate; C55=Isoprenoid Lipid Carrier; PEP=Phosphoenolpyruvate; AcCoA= Acetylcoenzyme A; I-V=Glycosyltransferases; UDP= Uridine 5'diphosphate; and GDP=Guanosine 5'-Diphosphate.

In addition, cell-free systems may be created from mutant organisms deficient in one or more of the enzymes of the xanthan biosynthetic pathway (for example, the pathway set forth in FIG. 12). Such mutant-derived cell lysates would produce the variant gums described herein, either due solely to the mutation or due to the mutation in combination with a withheld substrate. For example, a cell-free system created from a mutant culture lacking Transferase V would produce polytetramer while the same cell-free system, when no acetyl-CoA was present, would produce non-acetylated polytetramer.

The biosynthetic process may, in one embodiment, be monitored by the incorporation of radiolabeled substrates into the polymeric units. Other methods may also be used to allow identification of the biosynthetic intermediates that are known to those of ordinary skill in the art. In particular, chromatographic methods have been developed to separate and to identify the oligosaccharide intermediates. These include thin layer chromatography and high-performance liquid chromatography.

The cell-free biosynthesis of xanthan has been found to be a time-dependent, sequential process that is dependent on the addition of all three specific nucleotides. The background of non-specific incorporation of labeled substrate is minimal and does not interfere with the detection of the xanthan-specific polymer in the gum fraction.

The involvement of lipid carriers, specifically isoprenoid pyrophosphate, has been shown in several polysaccharide biosynthetic pathways. Additionally, the involvement of pyrophosphoryl-linked lipid carrier in xanthan biosynthesis has been demonstrated. Thus, the xanthan biosynthetic intermediates have been found to be recoverable in the organic soluble fraction with these carrier lipids. The recovered oligosaccharide can subsequently be freed from the carrier lipid by mild acid hydrolysis, for example, pH 2 for 20 minutes at 90° C. and dephosphorylated with alkaline phosphatase for analysis.

Using these methods for recovery of intermediate products, it has been discovered that, under in vitro conditions, certain lysates of *X. campestris* mutants will produce non-acetylated or non-pyruvylated xanthan gum even in the presence of all substrates required for non-variant gum synthesis. In light of the teachings herein, these methods will enable one skilled in the art to identify cell lysates which produce other altered polysaccharides.

In Vivo Polysaccharide Synthesis

The development of the cell-free synthesis process for the polysaccharides described above demonstrates that various *Xanthomonas campestris* cells have all the enzymes necessary to synthesize xanthan-based polymers that have the mannose residues acetylated, pyruvylated or unmodified. However, to use whole cells to synthesize polytetramer in vivo, a means for blocking xanthan gum synthesis at Reaction V (see FIG. 12) would be required. Moreover, in order for the whole cells to synthesize non-acetylated polytetramer, means for blocking the acetylation reaction (see FIG. 12) as well as reaction V would be required.

Furthermore, for whole cells to synthesize non-acetylated xanthan gum, a means of blocking the acetylation of either the Winner or outer mannose during xanthan gum synthesis would be required. Additionally, for the whole cells to synthesize non-acetylated, non-pyruvylated xanthan gum, a means of blocking xanthan gum synthesis at both the acetylation and pyruvylation 'steps would be required. In one embodiment of the present invention, mutagenesis was employed to alter some of the genes responsible for these various reactions.

Transposons, including but not limited to Tn10, TnK12 (Tn10 del16del17KanR), and Tn903, can be used to mutagenize *Xanthomonas campestris*. These transposons, in one embodiment, confer resistance to tetracycline or kanamycin. Transposons have the ability to insert themselves into genes wherein they cause mutations by interrupting the coding sequence. The transposons can be introduced into *Xanthamonas campestris* on various vectors, including on so-called suicide vectors, such as pRK2013. Vector pRK2013, as described by Ditta, G., Corbin, D. and Helinski, D. R. in Proc. Natl. Acad. Sci. U.S.A., 77:7347–7351 (1980), specifically incorporated herein by reference, has the ability to transfer itself into non-enteric bacteria, such as *Xanthomonas campestris*, but cannot replicate in that host. Thus, if the suicide vector is introduced into a population of *Xanthomonas campestris* cells and that population is subsequently challenged with either tetracycline or kanamycin, the individuals which survive are those in which one of the transposons has inserted into the genome of *Xanthonomas campestris*. Survivors of such a challenge can be screened for those which have lost the ability to make xanthan gum. Such mutants may appear less mucoid than mold-type *Xanthonomas campestris.*

In other embodiments of the invention, other means of mutagenesis can be employed to generate mutants that do not acetylate and/or pyruvylate the gums they produce. Such means will readily occur to one skilled in the art, and include, without limitation, irradiation, recombinant DNA technology (in particular, as described in U.S. patent application Ser. No. 07/333,868 of Capage et al., entitled "Recombinant-DNA Mediated Production of Xanthan Gum," filed Apr. 3, 1989, and incorporated specifically herein by reference, and in Example 1 below) and chemical mutagen treatment. Examples of such mutagenesis procedures have been described by Miller, J. H. in *Experiments in Molecular Genetics* (1972); Davis, R. W., Bostein, D. and Roth, J. R. in *Advanced Bacterial Genetics* (1980); and Maniatis, T., Fritsch, E. F. and Sambrook, J. in Molecular Cloning (1982), Cold Spring Harbor.

Although mutants can first be chosen which appear less mucoid than wild-type organisms, those desired generally retain the ability to make some polysaccharide. Cell-free extracts of each of the xanthan mutants can be prepared and tested as noted above by the addition of different combinations of substrates and analysis of the resultant products.

Alternatively, appropriate mutants can be detected by assaying the culture broth of each mutant for the presence of the desired polysaccharide, e.g., xanthan gum which has the outer mannose acetylated but not pyruvylated, pyruvylated but not acetylated, both pyruvylated and acetylated or unmodified while the inner mannose is acetylated or unmodified. Thus, mutants can be found which appear to be blocked at various positions of the xanthan gum pathway. On Jun. 28, 1989, Mutants of *Xanthomonas campestris* which produce xanthan gum that is acetylated at the inner mannose and acetylated at the outer mannose (X1397), acetylated at the inner mannose and pyruvylated at the outer mannose (X1398), acetylated at the inner mannose and unmodified at the outer mannose (X1399), unmodified at the inner mannose with a portion of the outer mannose moieties pyruvylated and a portion acetylated (X1400), unmodified at the inner mannose and acetylated at the outer mannose (X1401), and unmodified at the inner mannose and pyruvylated at the outer mannose (X1402), and unmodified at the inner mannose and unmodified at the outer mannose (X1403), were each placed on deposit at the American Type Culture Collection, Rockville, Md., under Accession Nos. 68033, 68034, 68035, 68036, 68037, 68038 and 68039, respectively. Mutant strains X1006, X921, and X934 were each placed on deposit at the American Type Culture Collection on Mar. 21, 1986, while mutant strain X1231 was deposited at the American Type Culture Collection on Mar. 9, 1987.

A mutant of *Xanthomonas campestris* which produces non-acetylated xanthan gum (X1006), a mutant which produces non-pyruvylated xanthan gum (X921), a mutant which produces xanthan gum containing low levels of pyruvylation (less than 5% of the terminal mannose X934), and a mutant which produces non-acetylated, non-pyruvylated xanthan gum [X1231(p41KS22)] have each been placed on deposit at the American Type Culture Collection Rockville, Md., under Accession Nos. 53472, 53473, 53474 and 67344 respectively.

Mutants of *Xanthomonas campestris* which produce variants of xanthan gum and which contain chromosomal mutations have also been produced, by way of example only, X1910 is described in Example 5 which produces polymer unmodified at the inner mannose and pyruvylated at the outer mannose. Strain X1910 was placed on deposit at the American Type Culture Collection, Rockville, Md., on Nov. 4, 1997, under Accession No. 202034.

It is not beyond the scope of the invention to employ enzyme inhibitors of Acetylase I, Acetylase II, Transferase V, and Ketalase to arrive at the same products. Still other alternatives for producing this family of polysaccharides are contemplated, including enzymatic and chemical degradation of natural xanthan gum.

The mutants can be grown under conditions generally known in the art for growth of wild-type *Xanthomonas campestris*. For example, they can be grown on suitable assimilable carbon sources such as glucose, sucrose, maltose, starch, complex carbohydrates such as molasses or corn syrup, various organic acids and the like. Mixtures of carbon sources can also be employed. The concentration of carbon source supplied is often between 10 and 60 grams per liter. Also necessary for growth are an assimilable source of organic or inorganic nitrogen, generally between about 0.1 and 10.0 grams per liter, and minerals, the choice of which are easily within the skill of the art. Examples of suitable nitrogen sources are ammonium salts, nitrate, urea, yeast extract, peptone, or other hydrolyzed proteinaceous materials or mixtures thereof. Examples of suitable minerals include phosphorus, sulfur potassium, sodium, iron, magnesium; these are often added with a chelating agent such as EDTA or citric acid.

Optimal temperatures for growth of *Xanthomonas campestris* generally are between 18° and 35° C., preferably between about 27° and 30° C. *Xanthomonas campestris* cells are grown aerobically by supplying air or oxygen so that an adequate level of dissolved oxygen is maintained, for example, above about 10% of saturation. Preferably, the level is kept above about 20%. The pH often is maintained at about 6.0 to 8.0, preferably at about 6.5 to 7.5.

The polysaccharides of the present invention can be recovered from fermentation broths by a suitable means. Precipitation with isopropanol, ethanol, or other suitable alcohol readily yields the polysaccharides of this invention. Generally, alcohols are added to a concentration of about 50 to 75%, on the basis of volume, preferably in the presence of potassium chloride, sodium chloride or other salt. Alternatively, the polymers can be recovered from the broth by ultra-filtration.

Mobility control solutions for use in enhanced oil recovery may also be prepared from the variant polysaccharide polymers disclosed herein. Solutions of the polysaccharide polymers at concentrations of from about 50 to about 3000 ppm are appropriate for such mobility control solutions. Other known additives may also be used in combination with these solutions to further enhance oil recovery. Such additives include, for example, surfactants, alkaline agents or metal or organic crosslinking agents.

The polysaccharide polymers, like xanthan gum, can also be used as thickening agents in foods, cosmetics, medicinal formulations, paper sizing, drilling muds, printing inks, and the like and as a gelling agent. In addition, they can be used to reduce frictional drag of fluid flow in pipes.

EXAMPLES

The following examples illustrate certain of the preferred embodiments of the present invention. All United States patent applications and other references cited in these Examples are specifically incorporated herein by reference.

Example 1

This example demonstrates that there are two *X. campestris* genes which encode enzymes that catalyze acetylation of xanthan gum.

Figure 1A:
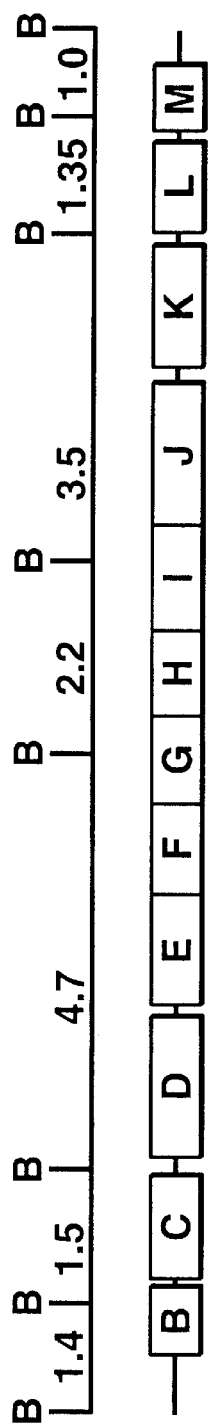
FIG. 1a shows the BamHI restriction map of a 16 kb region of the chromosome of X. campestris that contains a cluster of twelve genes required for biosynthesis of xanthan and also shows the approximate locations of these twelve genes relative to the BamHI restriction map.

Capage et al., U.S. patent application Ser. No. 07/333,868, described the nucleotide sequence of a 16 kb segment of *X. campestris* DNA that contains a gene cluster required for xanthan gum biosynthesis. Mutations were isolated that inactivated each of the genes identified by the DNA sequence. The phenotypes of mutant strains carrying these mutations were determined. Mutations in gene gumF (see FIG. 1a), caused by transposon insertion, resulted in production of xanthan gum that contained no detectable acetate. Insertion mutations in gene gumG did Rot result in any obvious defect in xanthan gum biosynthesis. Mutants with gene gumG defects produced high levels of xanthan gum, and this gum contained all of the normal constituents of xanthan in approximately normal molar ratios. On the basis of these initial results, it was concluded that gene gumF encoded as enzyme that catalyzed the known acetylation of the inner mannose of xanthan, while the activity of the gene gumG protein remained unknown.

However, when the DNA sequence was used to predict the amino-acid sequences of the products of genes F and G (gpF and gpG), these proteins were found to have extensive homology to one another. This finding indicated that the functions of gpF and gpG might be similar. The phenotypes of mutants defective in gene gumG were subsequently reexamined, and the compositions of xanthans produced by these mutants were precisely quantitated. These data showed a small (5%–10%) but significant decrease in the acetate content of gum produced by G⁻mutants as compared to wild-type X. campestris. Therefore further experiments were performed Ito determine what role gpG might have in acetylation of xanthan.

The hypothesis that gpG normally directs 10% of the acetylation of xanthan gum was seemingly contradicted by the observation that transposon insertion mutations in gene gumF resulted in elimination of acetylation. Clearly, these mutant gums did not retain 10% of the normal acetate content. However, it was possible that insertions in gene gumF reduced or eliminated the expression of gene gumG as a result of so-called "polar" effects. Insertions of Tn10 generally reduce expression of genes located downstream, in terms of transcription, from the insertion site as reported by Kleckner, N. et al., in J. Mol. Bio. 97:561–575 (1975). Moreover, the reduction can be quite severe in instances where the downstream gene is "translationally coupled" to the gene containing the insertion mutation as reported by Oppenheim, D. S. and Yanofsky, C., in Genet. 95:785–795 (1980). Translational coupling is a phenomenon wherein the translational stop signal of one gene overlaps the translational start signal of an adjacent downstream gene. In some cases where such coupling occurs, the initiation of translation of the downstream gene is largely or entirely dependent on termination of translation of the upstream gene occurring at the coupler. Thus, insertions in the upstream member of the coupled genes can dramatically reduce, or even eliminate, expression of the downstream gene because these inserts invariably cause frame shifting and premature termination of translation of the upstream gene.

Figure 1B:
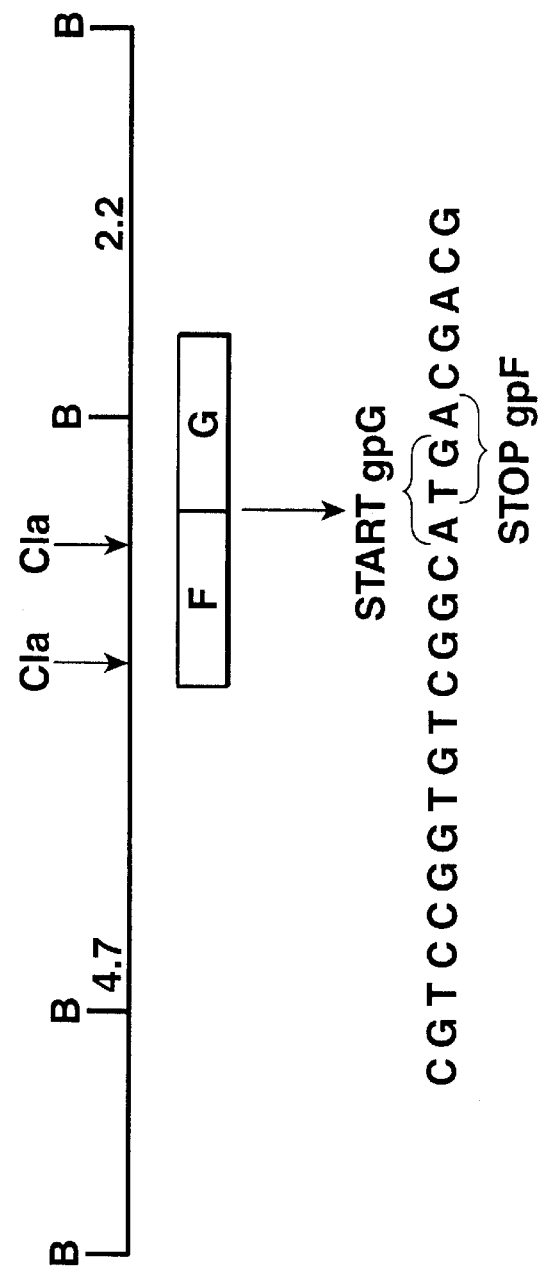
FIG. 1b shows some restriction sites in and around genes F and G and the DNA sequence at the junction of genes F and G.
Figure 2:
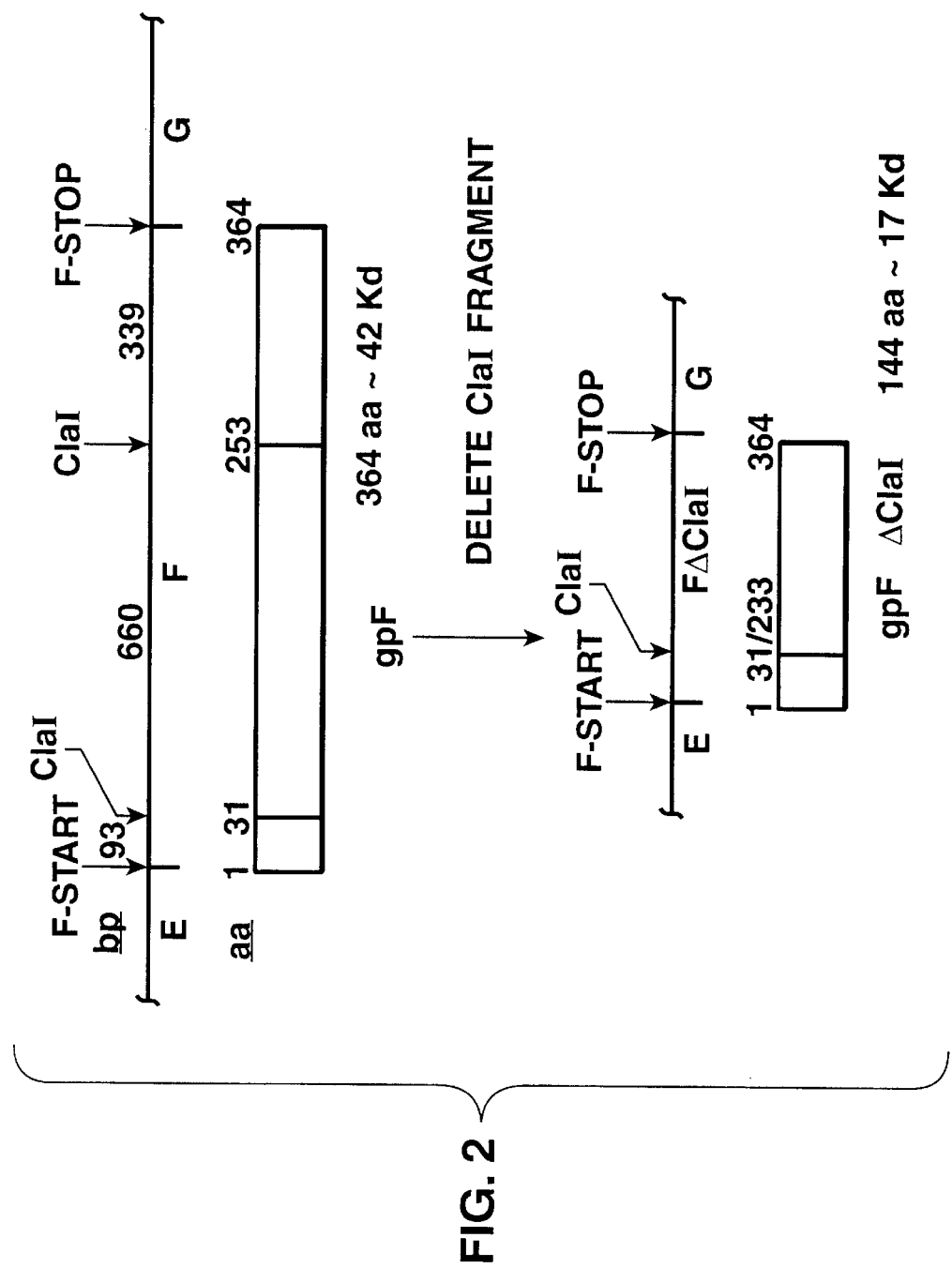
FIG. 2 depicts the construction of a deletion mutation (delCla) within gene gumF of the gum gene cluster.

The DNA sequence of the gum gene cluster revealed that the translational stop of gene gumF does overlap the translational start of gene gumG, i.e., the two are "coupled" (see FIG. 1b). Moreover, the sequence of the translational initiation signal for gene gumG is not particularly strong, which suggests that the translational coupling might play a significant role in gene gumG expression. To test this hypothesis, a deletion mutation (as shown in FIG. 2) was constructed within the coding sequence of gene gumF. This deletion eliminated 660 base pairs between the ClaI sites within gene gumF. The deleted DNA falls entirely within the coding sequence of gene gumF, and no foreign DNA is inserted. Thus, the deletion removes a large portion (approximately 60%) of the gene but does not alter the reading frame since the number of base pairs deleted is evenly divisible by 3. The mutant gpF produced by this deletion mutation (gpFdel) is missing 220 amino acids out of a total of 364, but the translational start of gene gumF and the gene gumF translational stop, coupled to the start of gene gumG, remain unaltered. The elimination of two-thirds of the amino acid residues of gpF is very likely, although not certain, to result in elimination of all protein activity. Thus, any residual acetylase activity from this mutant is most apt to be due to activity of gpG.

Figure 3A:
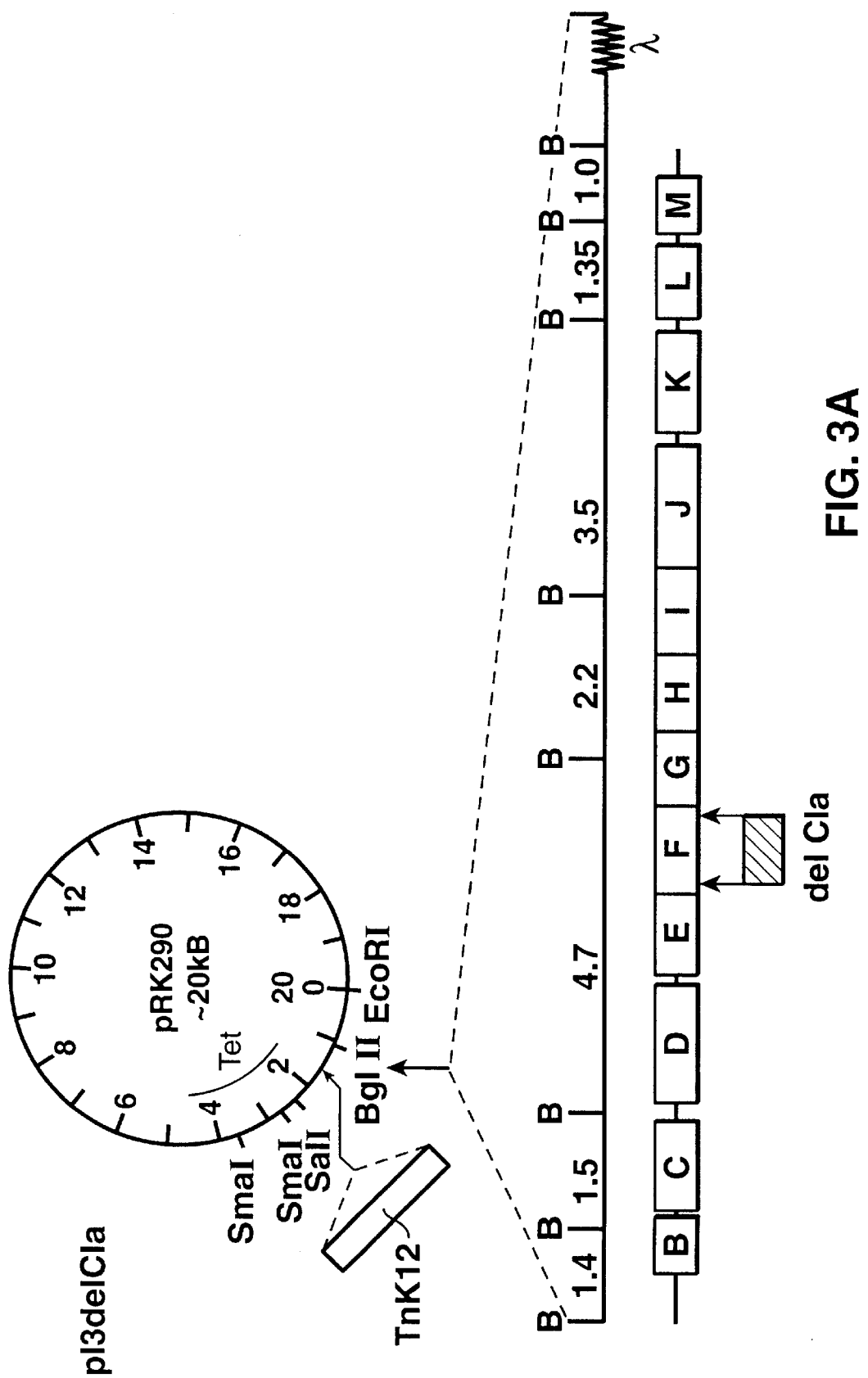
FIG. 3a shows the structure of plasmid p13delCla derived from pRK290-H336 by in vivo insertion of transposon TnK12 into the vector portion of pRK290-H336 in the approximate location shown in the figure and the subsequent deletion as described in FIG. 2 of the 660 base pair ClaI DNA fragment within gene gumF.

This ClaI deletion mutation was constructed on plasmid pRK290-H336.13 (FIG. 3a) which carries an otherwise wild-type gum gene cluster and an insertion of transposon Tn10 del16 del17 KanR described by Way et al., in Gene 32:369–379 (1984) and here termed TnK12, located within the vector position of the plasmid. The TnK12 insertion provides convenient drug resistances for selection of plasmid transfer. The deleted plasmid, termed p13delCla, was transferred into the X. campestris Gum⁻ deletion strain X1231, which is missing genes B–M, and polysaccharide produced by the resulting strain X1231(p13delCla) was analyzed. This gum contained a low but significant amount of acetate; roughly (10–15)% the amount normally found in wild-type xanthan.

Figure 3B:
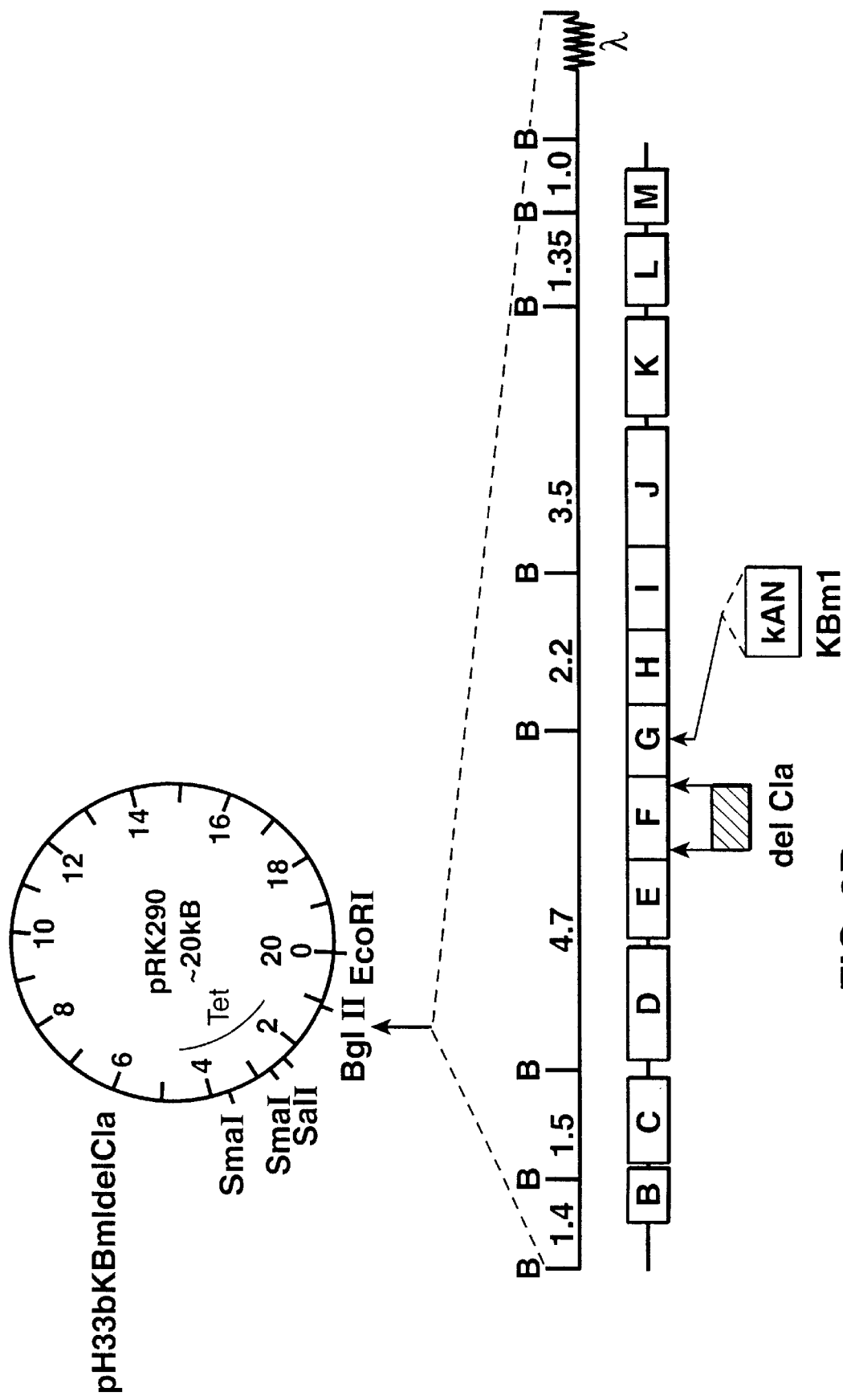
FIG. 3b shows the structure of plasmid pH336KBm1delCla which is similar in structure to p13delCla, containing the same ,660 base pair deletion within gene gumF. This plasmid contains an insertion mutation (KBm1) at the BamHI site within gene gumG. The DNA fragment inserted there is a SI restriction fragment carrying the kanamycin-resistance gene of plasmid pUC4-K.

This result indicated that both gpF and gpG are acetylases and that the bulk of acetylation of xanthan is catalyzed by gpF with a minor component of xanthan acetylation being catalyzed by gpG. However, it remained a possibility that the low level acetylation observed in the mutant X1231 (p13delCla) resulted not from the activity of gpG, but from a residual activity of gpFdel. To address this issue, a double mutant derivative of plasmid pRK290-H336 was constructed. As shown in FIG. 3b, this double mutant combined the gene gumF ClaI deletion mutation and an insertion mutation (KBm1) in gene gumG. The double mutant plasmid pH336KBmldelCla was transferred into strain X1231, and the polysaccharide produced was analyzed. If the low level acetylation observed in gum produced by X1231 (p13delCla) results from the activity of gpG, then the double mutant X1231(pH336KBmldelCla) should eliminate gpG activity by virtue of the insertional mutation in gene gumG, and no acetylation should be observed. If, however, the real source of acetylating activity in X1231(p13delCla) is the mutant gpFdel, the addition of the gene gumG insertion should not affect acetylation, and the same 10% level observed in X1231(p13delCla) should be seen in gum produced by the double mutant strain. The polysaccharide produced by strain x1231(pH336KBmldelCla) was found to contain no acetate. This proved that gpG does catalyze acetylation of xanthan and that, in wild-type strains, gpG is responsible for roughly 10% of the total acetylation that is observed.

Example 2

This example demonstrates that the target residue for acetylation by gpG (but not gpF) is the outer mannose of the xanthan repeating unit and that this acetylation is enhanced when pyruvylation of the outer mannose is blocked.

Mutations in gene gumL (FIG. 1a) of the xanthan biosynthetic gene cluster were previously shown to inactivate the ketalase enzyme which catalyzes pyruvylation of the outer mannose. Mutants lacking gpL activity produce xanthan gum devoid of pyruvate. However, initial studies of such mutants revealed that these non-pyruvylated polymers contained unusually high levels of acetate, generally >0.8 acetate/mannose. Thus, the outer mannose can be efficiently acetylated when pyruvylation is genetically blocked and further studies have shown that this acetylation is catalyzed by gpG and not gpF.

In order to examine the interaction of the two acetylase genes with the ketalase gene and each other, a set of eight mutant strains comprising all combinations of mutations in gene gumF (Acetylase I), gene gumG (Acetylase II), and gene gumL (Ketalase) were constructed. The various combinations of mutations were constructed on plasmid pRK290-H336 which contains the entire gum gene cluster.

The gene gumF mutation employed in these constructions is the in-frame deletion within this gene. As described above, this deletion eliminates 660 base pairs between the ClaI sites located within gene gumF. The deleted DNA falls entirely within the coding sequence of gene gumF, and no foreign DNA is inserted. Thus, the deletion removes a large portion (approximately 66%) of the gene but does not alter the reading frame since the number of base pairs deleted is evenly divisible by 3. The mutant gpF produced by this deletion mutation (gpFdel) is missing 220 amino acids out of a total of 364, but the translational start of F and its translational stop coupled to the start of G remain unaltered. The elimination of two-thirds of the amino acid residues of gpF was shown above to eliminate gpF activity.

The gene gumG mutation used in these mutants is an insertion (KBm1) within gene gumG at a BamHI site that interrupts the coding sequence of gene gumG. The inserted DNA is a restriction fragment containing the 1.3 kb Kan$^r$ DNA segment of plasmid pUC4-K as described by Vieira, J. and Messing, J., in Gene 19:259–268 (1982), which is ultimately derived from the kanamycin resistance gene of transposon Tn903.

The gene gumL mutations used were of two types. One is an insertion of transposon TnK12 within the coding region of gene gumL. The second type is derived from this insertion by deletion of a 3 kb HindIII fragment of TnK12 which carries the genes encoding resistance to kanamycin and streptomycin. In this TnK12 deletion mutation, an insert of 1 kb of TnK12 DNA still remains within the gene gumL coding sequence and this results in insertional inactivation of the gene gumL product.

The various combinations of these mutations were constructed on plasmid pRK290-H336 using in vitro recombinant DNA technology. The eight mutant plasmids obtained were then conjugally transferred from E. coli into X. campestris strain X1231 which contains the deletion mutation that eliminates the entire gum gene cluster from the chromosome. The 8 resulting strains X1396-X1403 (Table 1) were then analyzed for polymer production.

TABLE 1

| | Genotype | | |
|---|---|---|---|
| Strain | Acetylase I | Acetylase II | Ketalase |
| X1396[a] | + | + | + |
| X1397 | + | + | –[b] |
| X1398 | + | –[c] | + |
| X1399 | + | –[c] | –[d] |
| X1400 | –[e] | + | + |
| X1401 | –[e] | + | –[b] |
| X1402 | –[e] | –[c] | + |
| X1403 | –[e] | –[c] | –[d] |

[a]wild-type, carries TnK12 insertion within pRK290 portion of the plasmid
[b]TnK12 insertion mutation
[c]Kan$^r$ fragment insertion mutation
[d]TnK12 deletion derivative insertion mutation
[e]in-frame, non-polar deletion mutation All strains were grown in 50 ml each FXC-RAH-1 medium at pH 7.0 that contained:
  3.2 g/l N-Z-amine AS
  1.7 g/l MgSo$_4$.7H$_2$O
  0.7 g/l KH$_2$PO$_4$
  40 g/l glucose
  19.5 g/l (2-(N-morpholino) ethane sulfonic acid)
  5–10 mg/l kanamycin
  1 mg/l Tetracycline (where applicable) in 300 ml baffled shake flasks. Temperature was maintained at 30° C. After approximately 60 hours of incubation, the culture broths were diluted with two to four volumes of distilled H$_2$O and the cells removed by centrifugation at 14,000–18,000×g for 30 minutes at 10° C. Gums were precipitated from the supernatants by the addition of 2–3 volumes of 2-propanol and collected by centrifugation using the conditions described previously. The precipitates were then rehydrated in 100–300 ml of 20 mM NaCl and the precipitations repeated. The gums were finally rehydrated in 100 ml distilled H$_2$O each. Samples of each were subsequently dialyzed against 4 l of distilled H$_2$O for four days with daily H$_2$O changes in 12,000–14,000 MW cutoff cellulose tubing.

Triplicate samples of each purified gum were then concentrated 3–4-fold by vacuum drying and hydrolyzed in 2 M trifluoroacetic acid at 120° C. for 2½ hours. After neutralization with 1.2 M Na$_2$CO$_3$, the hydrolysates were filtered through 0.45 mim filters and ready for analysis by high-performance liquid chromatography (HPLC). The analyses were performed using a Beckman HPLC equipped with an Aminex HPX-87H ion exclusion column (300×7.8 mm). Organic acids were detected by ultraviolet absorbance at 214 nm. Refractive index was used to detect neutral sugars. The column was run isocratically with 0.01 N H$_2$SO$_4$ as the mobile phase at a flow rate of 0.6 ml/minute at 45° C.

The molar ratios of the components in each hydrolysate were calculated using a series of calibration curves based on peak areas for each sugar and organic acid.

The molar ratios of acetate and pyruvate to mannose are shown in Table 2.

TABLE 2

Molar Ratios of Acetate and Pyruvate to Mannose

| Strain | Acetylase I | Acetylase II | Ketalase | Acetate/Mannose | Pyruvate Mannose |
|---|---|---|---|---|---|
| X1396 | + | + | + | 0.66 | 0.43 |
| X1397 | + | + | – | 1.01 | 0.00 |
| X1398 | + | – | + | 0.63 | 0.36 |
| X1399 | + | – | – | 0.51 | 0.00 |
| X1400 | – | + | + | 0.10 | 0.39 |
| X1401 | – | + | – | 0.47 | 0.00 |
| X1402 | – | – | + | 0.00 | 0.37 |
| X1403 | – | – | – | 0.00 | 0.00 |

The following key observations about the data presented in Table 2 can be made.
1. The 660 bp deletion in gene gumF inactivated the gene F protein (Acetylase I). See X1402 vs X1398.
2. The gene gumG protein (Acetylase II) acetylated xanthan and at a much reduced level compared to wild-type when Ketalase was active. See X1400 vs X1396, described in Ex. 4.
3. If Ketalase was inactivated, acetylation by Acetylase II increased dramatically (X1400 vs. X1401), described in Ex. 4.
4. The extent of acetylation by Acetylase I did not increase in response to the inactivation of Ketalase. See X1398 vs X1399, described in Ex. 4.

5. Pyruvylation did not vary significantly regardless of the extent of acetylation. See X1396, X1398, X1400, and X1402, described in Ex. 4.

These data indicate that the gene gumG protein (Acetylase II) catalyzes the acetylation of the external mannose of xanthan. This appears to occur to a limited extent when Ketalase is active, but increases dramatically in Ketalase⁻ mutants. These data indicate that pyruvylation blocks acetylation, but the converse is not true since pyruvylation didn't change significantly regardless of the level of acetylation. The gene gumF protein (Acetylase I) catalyzes the acetylation of the internal mannose only, and previous data polytrimer and polytetramer variants of xanthan U.S. Pat. No. 4,713,449 and U.S. application Ser. No. 844,335 have shown that Ketalase catalyzes the pyruvylation of the external mannose only.

Example 3

This example demonstrates that gpG (Acetylase II) does not catalyze acetylation of the inner mannose of the xanthan repeating unit.

Figure 4:
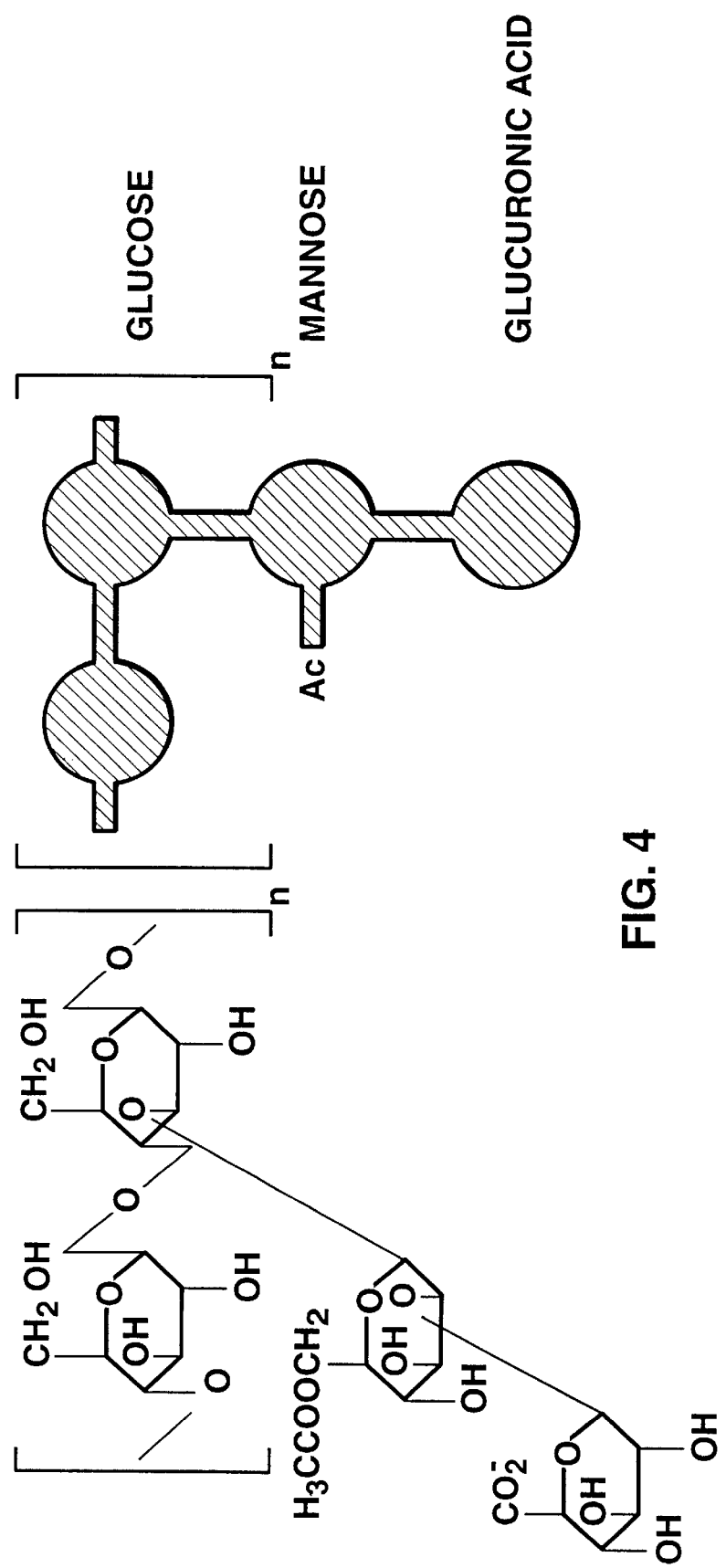
FIG. 4 depicts the chemical structure, and a schematic representation, of the repeating unit of the polytetramer variant of xanthan gum.
Figure 5A:
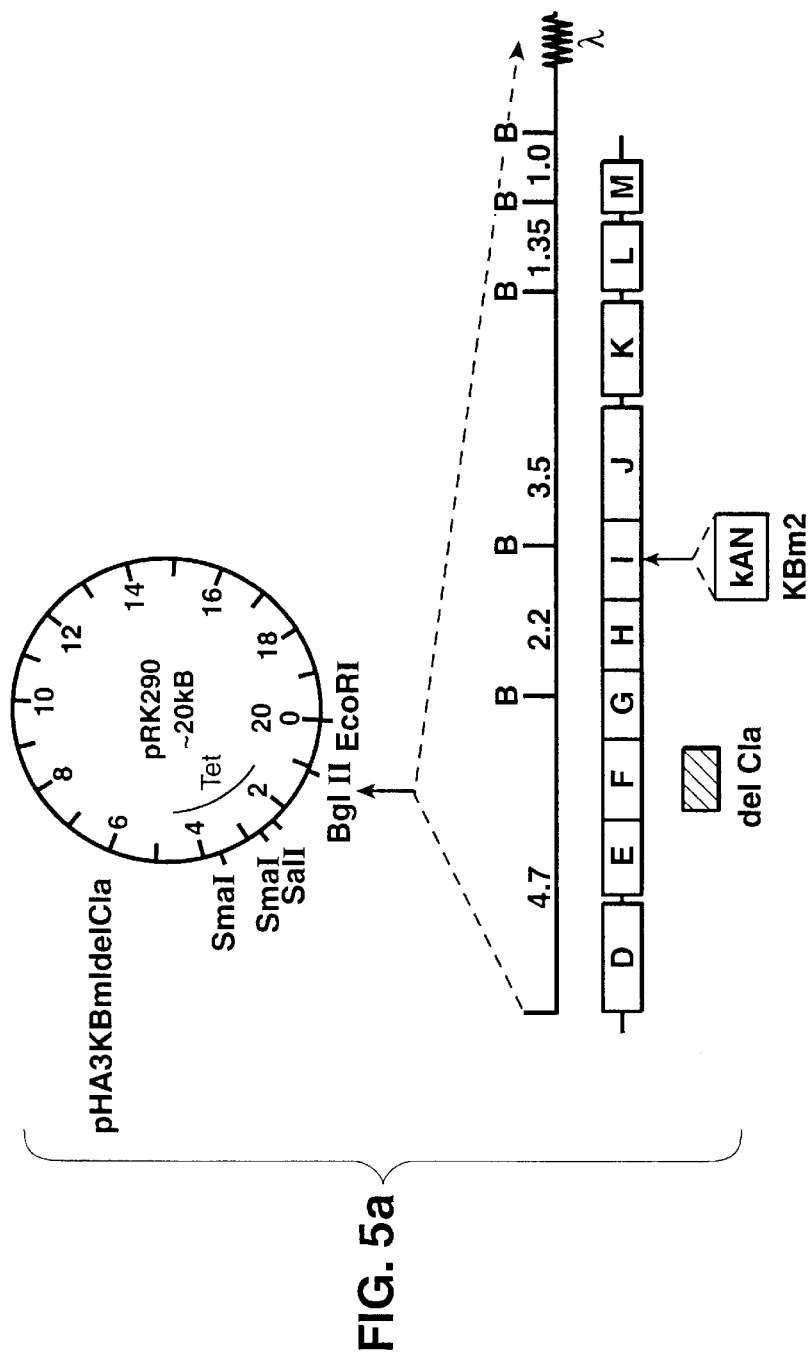
FIG. 5a shows the structure of plasmid pHA3KBm2delCla derived from pRK290-HA3 which is identical to pRK290-H336 except that-it does not contain the 1.4 kb and 1.5 kb SUSHI fragments of the X. campestris gum biosynthetic operon DNA and therefore lacks genes B and C but contains genes D through M. pHA3KBm2delCla contains the gene gumF deletion mutation described in FIG. 2 and an insertion mutation in the BamHI site of gene gumI. The inserted DNA is again a BamHI restriction fragment of pUC4-K which carries a gene conferring kanamycin resistance.
Figure 5B:
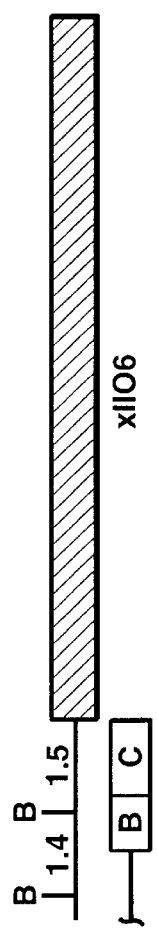
FIG. 5b shows the extent of a chromosomal deletion mutation present in X. campestris strain X1106 with genes 0 through M being deleted, while B and C are intact and functional in the chromosome.
Figure 6A:
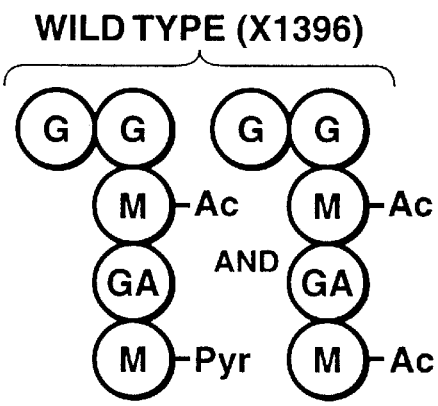
FIG. 6 depicts schematic representations of the structures of repeating units of the polysaccharides produced by wild-type X. campestris and mutants defective in genes F, G, or L and all possible combinations of mutations in genes F, G. and L. Abbreviations used are: G=glucose; M=mannose; GA=glucuronic acid; Ac=acetate; Pyr=pyruvate.
Figure 6B:
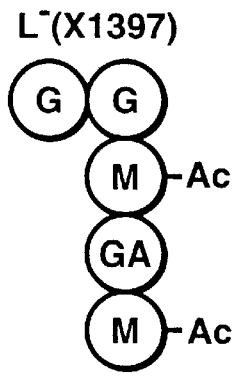
Figure 6C:
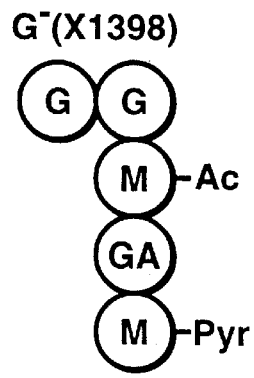
Figures 6D, 6E:
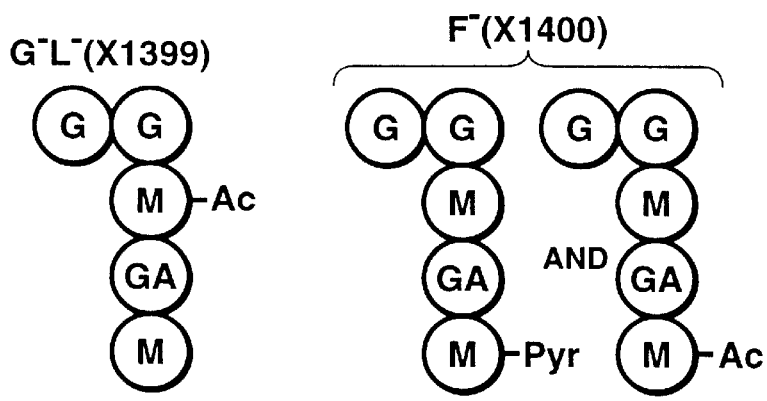
Figure 6F:
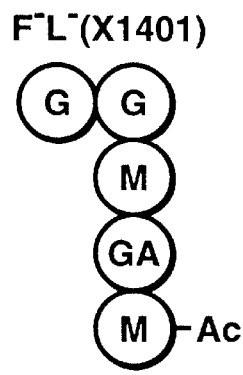
Figure 6G:
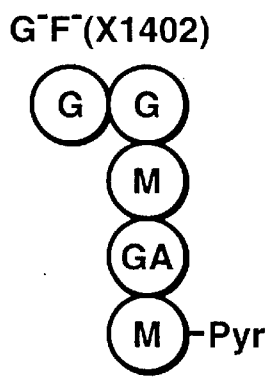
Figure 6H:
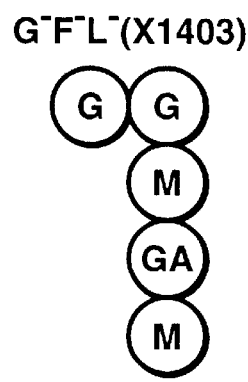

Gene I of the gum gene cluster encodes Transferase V (FIG. 1), the enzyme that adds mannose to the lipid-linked tetrasaccharide intermediate in xanthan biosynthesis. This system is described in U.S. Pat. No. 4,713,449. Mutations that inactivate gene gumI lead to the synthesis of a lipid-linked tetrasaccharide. This tetrasaccharide repeating unit is polymerized to yield polytetramer gum, which contains the internal mannose in its normal linkages but lacks the outer mannose normally found on xanthan gum (FIG. 4). A double mutant plasmid, pKBm2delCla, was constructed which contains an insertion mutation within gene gumI and the ClaI deletion mutation within gene gumF (see FIG. 5). The double mutant plasmid pKBm2delCla was transferred into the X. campestris deletion strain X1106 which contains only gum genes B and C in its chromosome. Genes B and C are provided by the chromosome since the mutant plasmid, derived from pRK290-HA3, does not carry B or C but contains all the remaining gum genes, D through M. The resulting strain, X1106(pKBm2delCla) or X1419, was analyzed for polymer composition twice. Both analyses failed to detect acetate in the polymer. This result shows that Acetylase II cannot acetylate the internal mannose Of the polytetramer to any significant degree. In this mutant strain, Acetylase II is active because gene gumG is not mutated and the gene gumF mutation is the non-polar ClaI deletion which has been shown above not to affect the expression of gene

Example 4

This example describes the repeating units that comprise the polysaccharide family that can be produced by genetic control of acetylation and pyruvylation of the pentasaccharide repeating unit of xanthan gum. The structures of these repeating units are shown in schematic form in FIG. 6.

(a) Wild-type (X1396); Acetylase I⁺, Acetylase II⁺, Ketalase⁺.

Normal xanthan is extensively acetylated at the inner mannose residue and is frequently pyruvylated on the outer mannose ;residue. Contrary to general belief, a significant percentage (10–20) of the outer mannose residues of normal xanthan are acetylated. Thus, normal xanthan repeating units are heterogeneous with respect to modifications of the outer mannose, containing either pyruvate or acetate.

(b) L⁻(X1397); Acetylase I⁺, Acetylase II⁺, Ketalase⁻.

This polymer contains no pyruvate and as a result is extensively acetylated at the outer mannose residue. The inner mannose residue is highly acetylated as in wild type.

(c) G⁻(X1398); Acetylase I⁺, Acetylase II⁻, Ketalase⁺.

This polymer is heavily acetylated on the inner mannose as in wild type, and the outer mannose is pyruvylated in the wild-type fashion. However, there is no acetylation of the outer mannose.

(d) G⁻, L⁻(X1399); Acetylase I⁺, Acetylase II⁻, Ketalase⁻.

This polymer has the high level wild-type acetylation of 1the inner mannose, but the outer mannose is unmodified.

(e) F⁻(X1400); Acetylase I⁻, Acetylase II⁺, Ketalase⁺.

The inner mannose of this polymer is unmodified, while the outer mannose is modified as in wild-type. That is, the outer mannose in generally pyruvylated, but a significant fraction of the outer mannose residues are acetylated instead.

(f) F⁻, L⁻(X1401); Acetylase I⁻, Acetylase II⁺, Ketalase⁻.

This polymer contains an unmodified inner mannose. The outer mannose is not pyruvylated but is heavily acetylated.

(g) F⁻, G⁻(X1402); Acetylase I⁻, Acetylase II⁻, Ketalase⁺.

This polymer is not acetylated at either the inner or outer mannose residues. Pyruvylation of the outer mannose occurs normally as in wild-type.

(h) F⁻, G⁻, L⁻(X1403); Acetylase I⁻, Acetylase II⁻, Ketalase⁻.

This polymer contains no acetate or pyruvate. Neither the inner nor the outer mannose residues are modified.

Example 5

This example describes the construction of a chromosomal deletion mutation defective in both acetylase genes gumF and gumG.

The variant xanthans described in Example 4 are produced by mutant strains of X. campestris in which the gum gene cluster has been deleted from the chromosome and is present in the cell on a recombinant plasmid. In some instances it might be desirable to have the gum gene cluster located in the X. campestris chromosome as this would eliminate the need for plasmid maintenance, and thus should improve strain stability. A chromosomal deletion mutation defective in genes gumF and gumG, which encode Acetylase I and II, respectively, was constructed as described below. This mutant produces non-acetylated xanthan gum.

FIG. 7a shows a map of a 4.3 Kb BglII fragment of the gum gene cluster that contains the gumF and gumG genes. This BglII fragment is cloned into the BglII site of the plasmid vector pSl to generate a recombinant plasmid termed pSlBgl. The pSl vector is a derivative of pRK290 in which the origin of vegetative, but not conjugal, DNA replication is replaced by the replication origin of pBR322. The pSl replication origin does not function a X. campestris. Therefore, pSl and its derivatives, such as pSlBgl are "suicide" plasmids, i.e., they can be conjugally transferred into X. campestris but cannot replicate in X. campestris.

The three ClaI sites shown in FIG. 7a were used in construction of the deletion mutation. Deletion of the ClaI fragment internal to the gumF gene was accomplished as described in Example 1 (by digesting pSlBgl with ClaI and religating at low DNA concentration) to produce pSlBglΔCla shown in FIG. 2b. In those experiments digestion at the third ClaI site within gene gumG was not observed, although the DNA sequence at this site is the ClaI recognition site, ATCGAT.

However, digestion by ClaI is known to be sensitive to methylation of the first adenine (A) residue of the recognition sequence. If that residue is methylated, the enzyme will not cleave the sequence. In E. coli, the sequence GATC is a substrate for the dam methylase which methylates the A residue of this tetranucleotide sequence. The ClaI recognition site in gene gumG is preceded by a G residue. Thus, in that sequence, GATCGAT, the underlined A is methylated because it occurs within the GATC tetranucleotide sequence; and therefore, the ClaI site is refractory to ClaI digestion.

In order to digest the ClaI site within gene gumG, it was necessary to produce unmethylated DNA by propagating pSlBgl∆Cla 1 in an *E. coli* dam strain which is defective for the relevant methylase activity. When unmethylated pSlBgl∆Cla DNA was prepared, digestion at the gene gumG ClaI was readily observed. Using this plasmid DNA as a substrate, the second ClaI fragment was deleted by digesting pSlBgl∆Cla with ClaI and religating at low DNA concentration to produce pSlBgl∆Cla2 which is shown in FIG. 7c. The resultant deletion of both ClaI fragments creates an in-frame fusion of the proximal portion of the gyps gene with the distal portion of the gumG gene. Therefore, transcription and translation through this region, and of distally located genes H through M (FIG. 1), should proceed normally.

Figure 8:
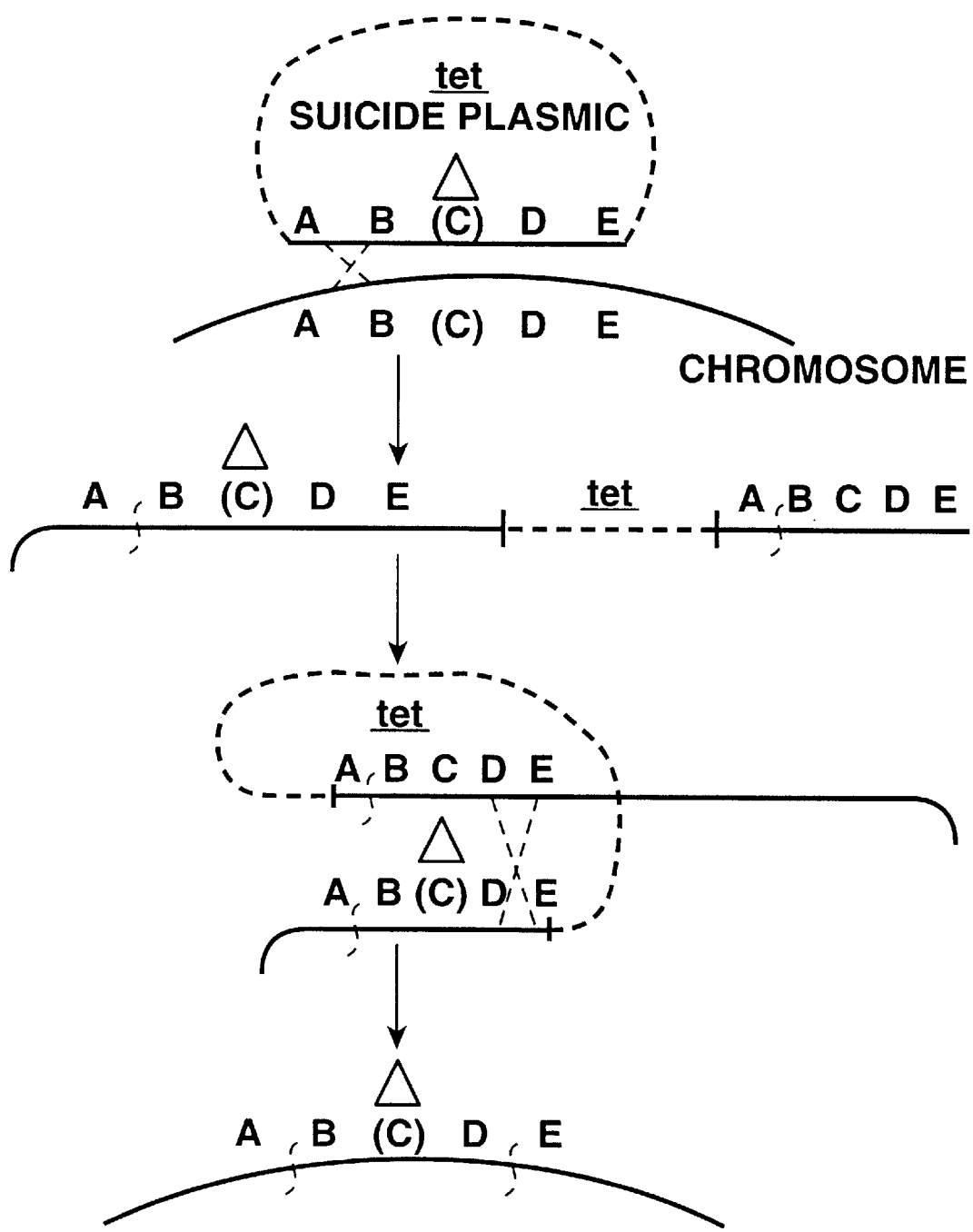
FIG. 8 shows the two-step recombination procedure as described in Example 5.

The plasmid pSlBgl∆Cla2 including the deletion mutation was transferred into the *X. campestris* chromosome via gene replacement. This two-step recombination procedure is diagrammed in a general fashion in FIG. 8. In general, in the first step, homologous recombination between the plasmid and the chromosome results in integration of the whole plasmid into the chromosome. This event is selected by selection for maintenance of an antibiotic resistance marker carried within the vector portion of the plasmid. In the second step, a subsequent recombination results in loss of the plasmid and retention of the constructed deletion mutation. This event is detected by the screening for loss of the antibiotic-resistance determinant and Southern blot hybridization analysis of chromosomal DNA structure.

In the present example, pSIBglΔCla2 was conjugally transferred into wild type *X. campestris* strain X77 by standard triparental matings and tetracycline-resistant transconjugants were selected. These tetracycline-resistant colonies were either light or dark yellow in appearance. DNA was prepared from four of each (light and dark type), digested with BamHI (pSIBglΔCla2 contains no SUSHI sites), separated by agarose gel electrophoresis and Southern blot hybridization was performed. Probing with labeled gum gene cluster DNA showed a wild type pattern in DNA from the light yellow isolates. The hybridization pattern for DNAs from the dark yellow isolates indicated that, in these isolates, pSIBglΔCla2 had recombined into the chromosome.

Two of the bonafide pSIBglΔCla2 insertion isolates were then grown in the absence of tetracycline to screen for the subsequent recombination in the second step of the gene replacement process. In these experiments, liquid cultures are grown to saturation in the absence of tetracycline, diluted 1:50 in fresh growth medium, and again grown to saturation. In several experiments of this type, the number of subculturing steps varied from 2 to 6.

Following the liquid subculturing steps, the cells were diluted and plated, in the absence of tetracycline, to yield isolated colonies. These colonies were tested for tetracyclineresistance. In different experiments, the frequency of tetracycline-sensitive colonies varied widely, from ~0.5% to >50%. The frequency of tetracycline-sensitive isolates increased with the number of generations of growth (i.e. subculture steps) in the absence of tetracycline.

Individual tetracycline-sensitive isolates were grown and their chromosomal DNAs analyzed by Southern blot hybridization to identify those isolates which contained the deletion mutation in the chromosome and had lost the plasmid sequences as a result of homologous recombination. One such isolate, termed X1910, was characterized for polysaccharide polymer production in vivo by the procedures detailed in Example 2.

The composition of the polysaccharide polymer produced by x1910 was found to be indistinguishable from wild type xanthan with respect to glucose, mannose, glucuronic acid and pyruvate; whereas, in contrast, no acetate was detected in the gum made by X1910. Thus this mutant produces non-acetylated xanthan having a composition equivalent to that produced by X1402 (Example 4), but does so as a result of the chromosomal deletion mutation. No recombinant plasmid or any foreign DNA is present in this strain.

The general approach and strategy described above could readily be applied to create analogous chromosomal deletion mutants that would produce any of the variant xanthans described in this application or in Vanderslice and Shannon U.S. Pat. No. 4,713,449.

Example 6

This example shows the methods of mutagenesis and screening employed to generate *X. campestris* mutant strains having defects in Acetylase or Ketalase activity.

The genes encoding the enzymes of xanthan gum biosynthesis have been shown to comprise a set of clustered genes on the *X. campestris* chromosome. This "gum gene cluster" has been described in detail by Capage et al. Segments of gum gene DNA have been cloned on plasmid vectors such as pMW79 as detailed in Capage et al.

Regionally-directed mutagenesis was performed upon subcloned portions of the gum DNA carried in plasmid pMW79. These cloned DNA segments were mutagenized in vivo with transposons and in vitro, by using recombinant DNA technology to generate insert;, deletion, and substitution mutations within the cloned *X. campestris* DNA. In order to study the phenotypes conferred by these mutations, the plasmids carrying the mutations were transferred back into *X. campestris* and subsequently recombinants were identified in which the plasmid-borne, mutated gene had been inserted in the chromosome via homologous recombination. The tetracycline resistance encoded by Tn10 affords a convenient selective system for movement of mutations from a plasmid into the chromosome.

One such mutant strain (X1006) carried a Tn10 insertion that was found to cause inactivation of the Acetylase activity. This mutant strain was characterized as described in Example 7 and 8, and found to produce a polysaccharide that was non-acetylated. A second mutant strain was constructed by the n vitro insertion of a fragment of DNA containing the tetracycline resistance gene of Tn10 into a restriction site within the gum gene cluster. This mutant strain (X921) was found to be defective in the Ketalase activity. As found by the methods of Examples 7 and 8, this mutant produced xanthan that was non-pyruvylated.

A third mutant strain (X934) was also found that greatly reduces the ketalase activity. This mutant strain produces xanthan gum that has a very low level of pyruvylation: 1–5% of the level of pyruvylation found in normal xanthan.

The mutant strain X934 was found as described below. In preliminary experiments designed to study recombination between plasmid-borne *X. campestris* DNA and the *X. campestris* PstI fragment cloned in plasmid RSF1010. This insertion of Tn10 causes the Gum- defect in the mutant strain X655 as described by Capage et al. and Vanderslice et al. The experiment was to mobilize PTX655 with plasmid pRK2013 and transfer it from *E. coli* into *X. campestris* by selecting for transfer of the tetracycline resistance encoded by Tn10. The initial results of this mating were anomalous and suggested that Tn10 did not express tetracycline resistance efficiently in *X. campestris* when carried on the plasmid, but that the drug resistance was more efficiently expressed when Tn10 was carried in the chromosome of *X. campestris*. This phenomenon has also been described for Tn10 in *E. coli*. There, it has been shown that strains carrying one copy of Tn10 inserted in the chromosome are resistant to significantly higher concentrations of tetracycline than are strains carrying Tn10 on a multicopy plasmid. The selection of Tet$^r$ *X. campestris* out of the above mating resulted in a high frequency (0.5 per recipient) of progeny which grew very poorly (i.e., only small, watery colonies) on tetracycline. After prolonged incubation, a Large fraction of the colonies (25%) produced sectors of more vigorously growing cells. More than 50% of these sectors appeared to be Gum- in morphology. These probably result from recombination between the plasmid-borne DNA containing the Tn10 insertion and the chromosomal wild type DNA. When the Tn10 is recombined into the chromosomal, high-level Tet$^r$ is obtained and the vigorously growing sector is observed. When these Gum-, Tet$_l$ sectors were picked and restreaked on tetracycline, they grew well and displayed a characteristic Gum- morphology.

Gum$^{+, Tet^r}$ isolates were also characterized. Some of these strains (in particular X934) were found to contain the entire plasmid pTX655 inserted into the chromosome of *X. campestris* via homologous recombination. The chromosomal structure of the X934 strain was determined by Southern blot hybridization of the chromosomal DNA which shows that the plasmid sequences exist in a chromosomally integrated form.

Example 7

This example shows how the altered polysaccharides of the present invention can be prepared in vitro. For instance, it shows how non-acetylated and/or non-pyruvylated xanthan gum was prepared in vitro.

Preparation of Lysates

*Xanthomonas campestris* B1459 S4-L or S4-L mutants described in Examples 6 and 10 were grown in YM (yeast-malt medium) supplemented with 2% (w/v) glucose as described by Jeanes, A. et al. in U.S. Department of Agriculture, ARS-NC-51, pp. 14 (1976), specifically incorporated hereby by reference. Cultures were grown to late log phase at 30° C. The cells were harvested by centrifugation and washed with cold Tris-HCl, 70 mM, pH 8.2 with 10 mM EDTA and were freeze-thawed three times by a procedure similar to Garcia, R. C. et al. described in European Journal of Biochemistry 43:93–105 (1974), specifically incorporated hereby by reference. This procedure ruptured the cells, as was evidenced by the increased viscosity of the suspensions and the complete loss of cell viability (one of 10$^6$ survivors) after this treatment. The freeze-thawed lysates were frozen in aliquots at −80° C. Protein concentration was determined with BIO RAD assay (BIO RAD Laboratories, Richmond, Calif.) and was found to be 5 to 7 mg cell protein per ml of lysate.

Biosynthetic Assay Procedure

As described by Ielpi, L. Couso, R. O., and Dankert, M. A. in FEBS Letters 130:253–256 (1981), specifically incorporated herein by reference, an aliquot of freeze-thawed lysate (equivalent to 300 to 400 ug protein), DNAase I (10 ug/ml), and MgCl$_2$ (8 mM) were preincubated at 20° C. for twenty minutes. An equal volume of 70 mM Tris-HCl, pH 8.2, with the desired radiolabled sugar nucleotides (UDP-glucose, GDP-mannose and UDP-glucuronic acid) were added and incubated at 20° C. Radiolabeled phosphoenol pyruvate and acetyl coenzyme A were added when desired as described in Ielpi et al., supra, and Ielpi, L. Couso, R. O., and Dankert, M. A. Biochem. Biophys. Res. Comm. 102:1400–1408 (1981) and Ielpi, L., Couso, R. O., and Dan Kert, M. A., Biochem. Intern. 6:323–333 (1983), both of which are specifically incorporated herein by reference. At various times, the reactions were stopped by dilution with 4° C. buffer. The samples were centrifuged and the pellets were washed two times with buffer. The supernatants were combined, carrier xanthan (100 ug) was added, and the xanthan plus synthesized polymer was precipitated with ethanol (60%)-KCl (0.8%). The precipitated polymer was resuspended in water and reprecipitated two more times to remove unincorporated label. Radioactivity incorporated into the precipitate (termed the gum fraction) was determined in d liquid scintillation counter and the data were processed to obtain incorporation in terms of picomoles of the radiolabeled components.

Cell lysates of X1006 did not incorporate carbon-14 acetate from [$^{14}$C] acetyl CoA into the gum fraction of the in vitro system. Cell lysates of S4-L did produce in vitro gum radiolabeled with [$^{14}$C] acetate. Similarly, cell lysates of X921 did not incorporate [$^{14}$C] pyruvate into the gum fraction while S4-L cell lysates did incorporate radiolabeled pyruvate from phosphoenol [$^{14}$C] pyruvate into the gum fraction of the in vitro system. Thus, X1006 was identified as a mutant strain with a defect in the gene for Acetylase and X921 as a mutant strain with a defect in the gene for Ketalase. Lysates of these strains produced non-acetylated xanthan and non-pyruvylated xanthan, respectively, in vitro.

It has also been shown that, by withholding substrates, *X. campestris* B1459 S4-L lysates produce altered polysaccharides in vitro. For example, cell lysates of S4-L did produce non-acetylated, non-pyruvylated xanthan gum in vitro when the endogenous acetyl-CoA and phosphoenolpyruvate were depleted.

A mutation in the gene for Transferase V would result in the production of polytetramer. This phenotype would be demonstrated by the A vitro method described above. The gum fraction would reveal a polysaccharide composed of glucose, mannose and glucuronic acid in molar ratios of 2:1:1. The tetrameric intermediate hydrolyzed from the lipid carrier would also be detected by its mobility on TLC and its molar ratio of sugars.

Example 8

This example demonstrates the use of the Acetylase-deficient strain, X1006, to produced non-acetylated gum in vivo. This example also demonstrates the in vivo production of the non-pyruvylated gum from the Ketalase-minus strain, X921, and xanthan gum with a reduced level of pyruvylation from the strain X934.

The three mutant strains described above and S4-L were grown overnight in broth with two percent glucose at 30° C. The gum was harvested by removing cells by centrifugation, precipitating the gum from the supernatant by addition of 2-propanol or ethanol with 0.5 to 1% potassium chloride. The gum precipitate was recovered by centrifugation and resuspended. The procedure was repeated. The resuspended gum was dialysed against water. A sample of each polysaccharide was acid hydrolyzed and analyzed by HPLC using a BIO RAD HPX-87H column. Xanthan components were quantitated by the injection of standards of known concentration.

The HPLC analysis of the hydrolyzed gums showed that X921 produced xanthan gum without pyruvate. Strain X1006 produced xanthan gum with no acetate. Strain X934 produced a gum that contained pyruvate at a level of 1–5% that of S4-L gum.

Example 9

This example describes methods and strategies that could be employed to construct mutants of *X. campestris* that will produce xanthan that is both non-acetylated and non-pyruvylated.

Mutant strains of *X. campestris* lacking Ketalase (X921) or Acetylase (X1006) activity have been described. One could use microbial genetics and recombinant DNA methods as described by Vanderslice et al. and Capage et al. to introduce a Ketalase defect and an Acetylase defect into a single strain of *X. campestris*. This double-mutant strain would produce xanthan gum that was both non-acetylated and non-pyruvylated.

Methods for producing insertion mutations into cloned gum gene DNA carried on plasmid vectors have been described by Capage et al. One could envision using a plasmid carrying the insertion mutation that gave rise to mutant strain X921 as a substrate for a second round of mutagenesis in vivo or in vitro. This second round of mutagenesis could employ any of a number of transposable elements that would readily occur to one skilled in the art or any of an equally obvious number of DNA restriction fragments containing selectable markers. A set of plasmids carrying two insertions mutations could be used in the gene replacement technique of Capage et al. to transfer the plasmid-borne mutations into the chromosome of *X. campestris*. Phenotypes of the resultant strains can be analyzed by the in vivo and in vitro techniques described by Vanderslice et al. and Capage et al., supra, in Example 7. These analyses will reveal doubly mutant strains that are blocked in both the Ketalase and Acetylase activity. These double mutant strains will produce xanthan that is simultaneously non-pyruvylated and non-acetylated.

Example 10

This example describes procedures to obtain a *X. campestris* mutant which produces polytetramer.

As describe above and in Vanderslice et al., supra, a xanthan-related polysaccharide with a truncated side chain, polytrimer, has already been obtained. This mutant was characterized by in vivo and in vitro methods described herein. Using the methods described herein and in the referenced patent applications, one versed in the art can create mutant strains of *X. campestris* which make polytetramer gum described above.

Identification of these mutant strains can be achieved using in vitro methods or by analysis of the polysaccharides produced in vivo, as described herein and in Capage et al., supra.

Once the polytetramer producing mutant has been obtained, additional mutational steps, such as those described in Examples 6 and 10 and generally known to those versed in the art, can be carried out to generate mutant strains which produce nonacetylated polytetramer.

Example 11

This example discusses cloning the acetylase gene and the ketalase gene onto vectors to ensure that the polysaccharides 'described herein are fully acetylated, fully pyruvylated, or both.

The *X. campestris* strains X1006 and X921 have mutations in the genes for acetylase and ketalase, respectively, as described in Examples 6 and 7. These mutants were created employing the methods described in Example 6. It is possible for one skilled in the art to employ methods described in Betlach et al., supra, to recover native DNA restriction fragments containing the Acetylase or Ketalase genes. That is, plasmids with DNA restriction fragments containing the Acetylase or Ketalase genes interrupted by a drug resistance marker can be used to probe Lambda genomic libraries to obtain native DNA sequences for the Acetylase or Ketalase gene. In another embodiment, the genes for the acetylase and ketalase enzymes have already been cloned onto the plasmid pRK290-H336, ATCC Accession No. 67049 as described by Capage et al., supra, and other plasmids described therein. It is a simple matter for those skilled in the art to subclone the Acetylase and Ketalase genes themselves from these plasmids.

The native DNA sequences obtained by either method can then be inserted onto plasmids capable of replication in *X. campestris*, for instance pMW79, using the methods revealed in Betlach et al. Expression of the Acetylase and/or Ketalase gene can be controlled by modifying the existing DNA sequence or inserting regulatable promoters upstream from the gene. Such techniques are well known to those versed in molecular biology and genetics. Similarly, the plasmids onto which the genes are inserted can be high copy number plasmids. As revealed in Capage et al., the xanthan biosynthetic enzymes are present in low amounts in *X. campestris*. Insertion of the plasmids described above into *X. campestris*, and growth of cultures under appropriate conditions for expression of the plasmid-borne genes, will result in synthesis of much greater numbers of the Acetylase and/or Ketalase enzymes than the other xanthan biosynthetic enzymes. Overexpression of the Acetylase should cause the xanthan polysaccharide to be fully acetylated, i.e., all internal mannose residues acetylated. Similarly, overexpression of the Ketalase should cause xanthan polysaccharide to be fully pyruvylated on the terminal mannose.

It should be evident to one skilled in the art that full acetylation and full pyruvylation of xanthan can be achieved by the methods described above. Furthermore, full acetylation of polytetramer, and full acetylation of polytrimer (described in Vanderslice et al., supra) can be achieved employing the methods described herein.

Example 12

This example demonstrates the economic and technical advantages of a non-pyruvylated polysaccharide produced by a genetically modified *Xanthomonas campestris* for viscosifying water at high temperatures.

Xanthan gum, a natural product of *Xanthomonas campestris*, is an effective viscosifier of water for use in, for example, enhanced recovery of petroleum. These viscosity applications frequently necessitate xanthan gum to be applied at high temperature and in saline brines. Xanthan gums are effective viscosifiers even at high temperature (for example, 75° C. to 100° C.), although their viscosity is substantially reduced over that at lower temperature (for example, 25° to 60° C.).

The inventors have discovered a new and novel polysaccharide produced by a genetically modified strain of *Xanthomonas campestris* (strain X921) that produced a viscosity at high temperature equal to that of wild-type xanthan gum produced from the S4-L parent strain (strain X237). This xanthan gum has the normal pentameric xanthan structure but, because of the genetic modification, contains no pyruvate moiety on the terminal mannose. This novel polysaccharide has low viscosity at fermentation temperature near 30° C. which will result in substantial cost savings and processing conveniences. The cost to produce pyruvylated xanthan gum is high primarily because the polymer's high viscosity requires great energy input for agitation, aeration and cooling.

Figure 9:
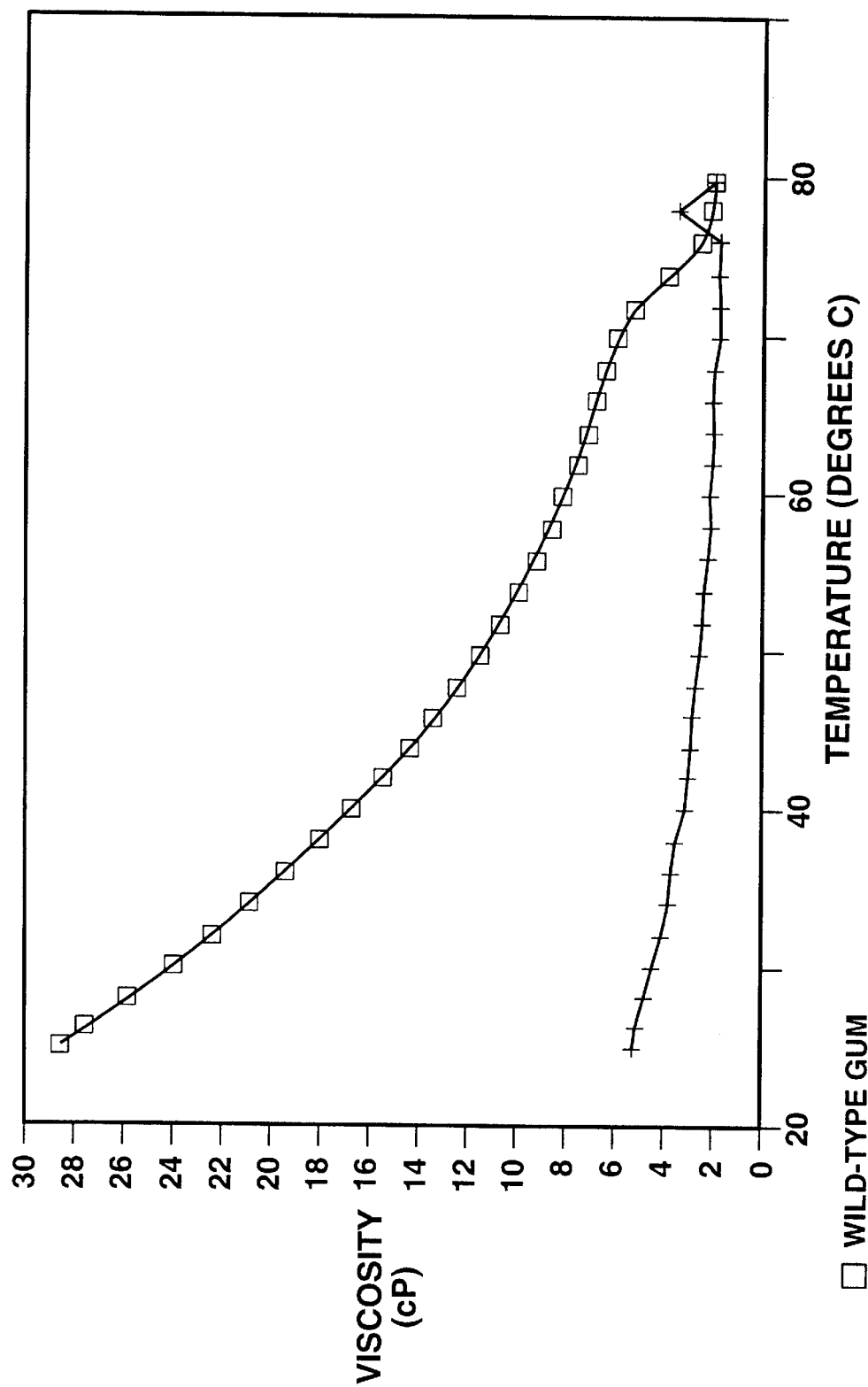
FIG. 9 depicts a viscosity comparison between wild-type and non-pyruvylated gums.

FIG. 9 shows a viscosity comparison of the novel non-pyruvylated xanthan gum to a wild-type xanthan gum produced by the unmodified parent. The wild-type gum shows high viscosity at low temperature but the viscosity decreases rapidly with increasing temperature. The non-pyruvylated gum, on the other hand, has lower viscosity at low temperature, but retains a viscosity at high temperature essentially equivalent to the wild-type xanthan gum. The viscosities reported in FIG. 9 were recorded at a shear rate of 8 $s^{-1}$ in a concentric cylinder viscometer on solutions of 1000 ppm active polymer solids in 5000 ppm NaCl brine.

Example 13

This example demonstrates the advantages of a non-acetylated xanthan produced by a genetically modified *Xanthomonas campestris* for use as a viscosifying agent for aqueous solutions.

Figure 10:
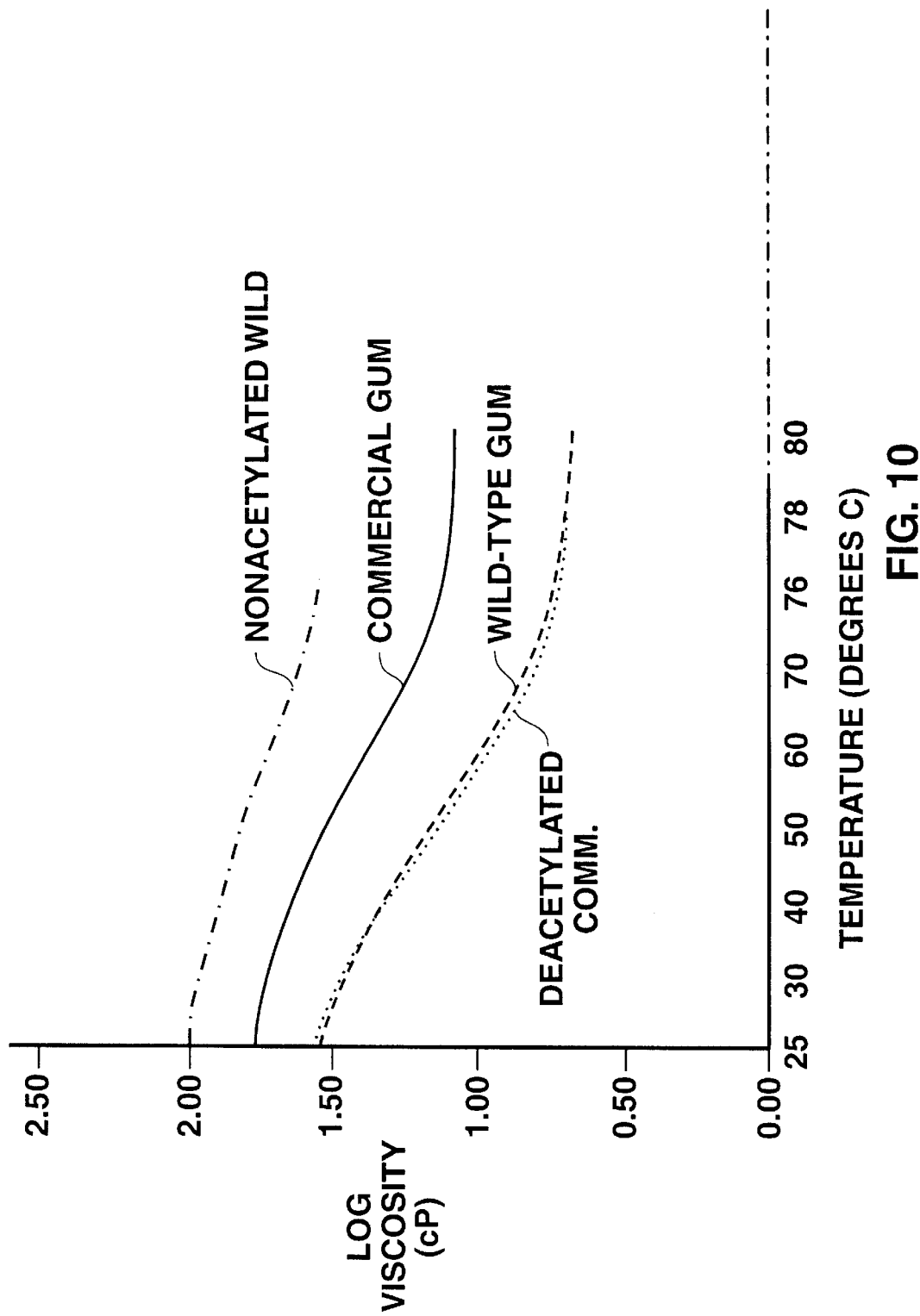
FIG. 10 depicts a viscosity comparison between non-acetylated and chemically-deacetylated gums.

FIG. 10 compares the viscosities of chemically deacetylated commercial xanthan and its parent compound with those of a non-acetylated xanthan polysaccharide made from a genetically manipulated *Xanthomonas campestris* (strain X1006) and of the xanthan gum made from the wild-type *X. campestris* parent (strain X237). The viscosities were obtained at a shear rate of 8 s for 1000 ppm polymer concentration in 50,000 ppm NaCl brine. Viscosities were measured over the temperature range of 25° C. to about 80° C.

FIG. 10 demonstrates that chemical deacetylation of xanthan results in a loss of viscosifying power over the entire temperature range. However, elimination of acetylation by genetic means results in substantially increased viscosity compared to the wild-type xanthan gum. Thus, non-acetylated xanthan gum produced by a mutant strain of *X. campestris* is an improved polysaccharide compared to the xanthan itself and compared to deactetylated xanthan gum produced by chemical methods.

Example 14

This example describes the methods used to construct a double mutant strain of *X. campestris* that produces non-acetylated, non-pyruvylated xanthan.

Figure 11:
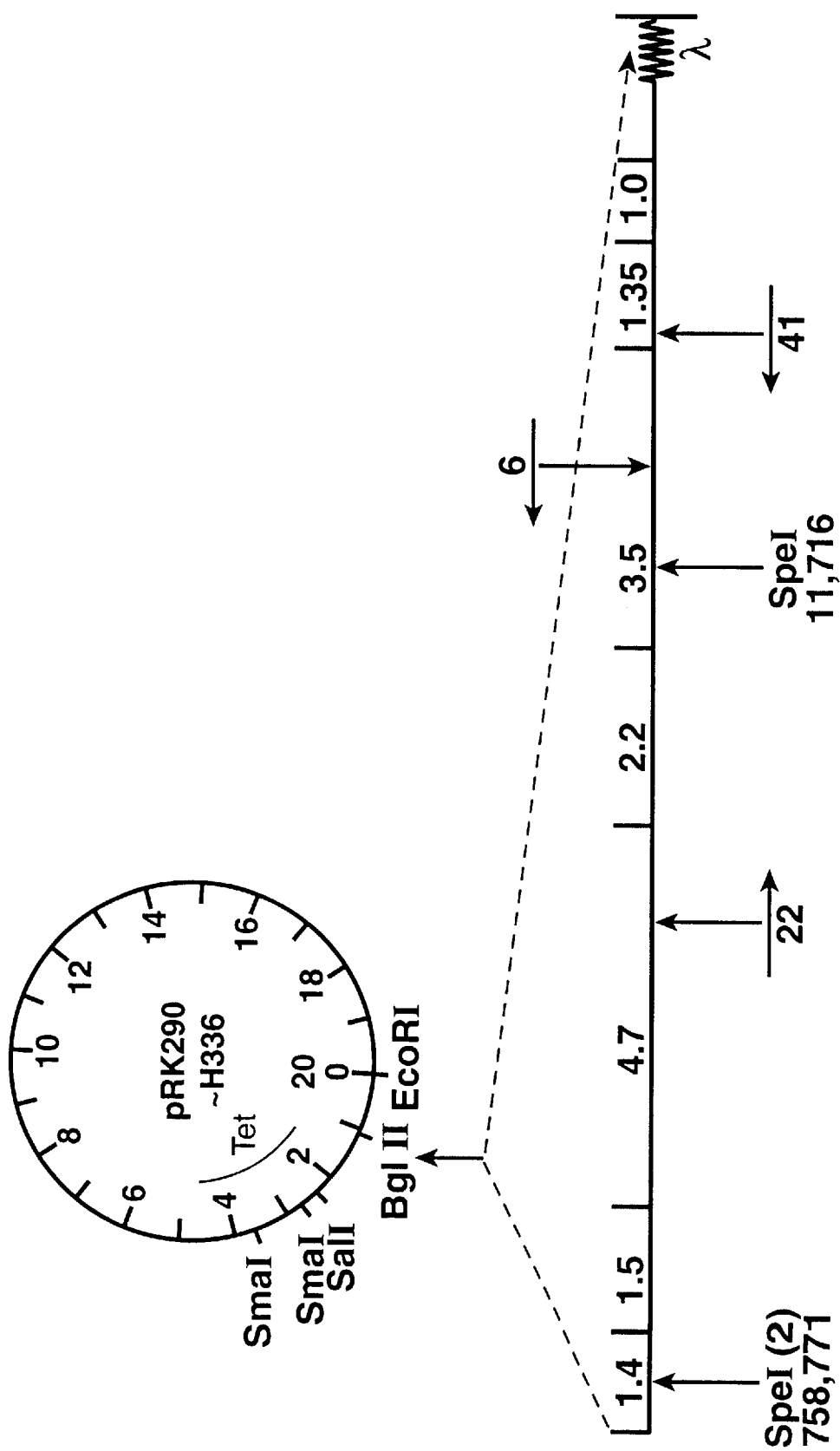
FIG. 11 depicts the approximate physical location of 3 TnK12 insertion mutations within the cloned gum gene cluster DNA of recombinant plasmid pRK290-H336. This figure also shows the approximate locations of SpeI restriction endonuclease cleavage sites in pRK290-H336.

Capage et al. have described the cloning of a gene cluster from *X. campestris* that contains genes that direct the biosynthesis of xanthan gum. They also described the isolation of chromosomal deletion mutations in *X. campestris* that eliminate all or varying portions of this gene cluster. One such deletion mutant, strain X1231, lacks all of the *X. campestris* DNA that is carried on the recombinant plasmid pRK290-H336. Thus, strain X1231 does not synthesize xanthan. When pRK290-H336 is transferred into strain X1231, the ability to synthesize xanthan is restored. Capage et al. also described methods of isolation and characterizing insertion mutations of transporon TnK12 within the cloned gum gene DNA carried on pRK290-8336. Two such mutant plasmids are pRX290-H336.22 and pRK290-H336.41. The approximate locations of the TnK12 inserts on each of these plasmids is shown in FIG. 11. When pRK290-H336.22 is transferred into X1231, the resultant strain produces non-acetylated xanthan. When pRK290-H336.41 is transferred into X1231, non-pyruvylated xanthan is produced. These two plasmid mutants have been used to construct, by means on in vitro recombination, a double mutant plasmid that directs synthesis of non-acetylated, non-pyruvylated xanthan when carried in the deletion strain X1231.

The in vitro strategy for generating a non-acetylated, non-pyruvylated double mutant plasmid is as follows. A kanamycin-sensitive (Kan$^s$) derivative of pRK290-H336.41 was generated by doing a partial HindIII digestion of the plasmid, ligating the digestion products at very low DNA concentrations (to promote intramolecular ligation), and then screening tetracycline-resistant (Tet$^r$) transformants for kanamycin sensitivity. Plasmid DNAs were then prepared from Tet$^r$, Kan$^s$ isolates and analyzed by restriction endonuclease digestion and agarose gel electrophoresis. There are only three HindIII sites in pRK290-H336.41, and two of these occur within TnK12 and bracket the Kan gene. Thus, a high proportion of the deletions generated in the partial digestion were deleted for the Kan gene whereas the rest of the plasmid was retained intact. The Kan$^s$ plasmid still carries an insertion (1 kb) in the ketalase gene and thus was expected to yield non-pyruvylated gum. This plasmid is termed p41KS. The next step was to clone the large SpeI fragment of the non-acetylated mutant plasmid pRK290-H336.22 into p41KS. As shown in FIG. 11, each plasmid contains three SpeI sites at positions 758, 771, and 11,716 within the DNA sequence so Capage et al. the 10.9 kb SpeI fragment carries the Tnk12 insertion of pRX290-H336.22. The small (13 bp) SpeI fragment lies entirely within a tRNA gene which is nonessential for *X. campestris* growth and xanthan production. Thus, deletion of this small SpeI segment in the process of the double mutant construction ought not to affect xanthan biosynthesis. Plasmids p41KS and pRK290-H336.22 were purified and digested to completion with SpeI and a ligation was performed. In this ligation, p41KS/SpeI was ligated in 10x molar excess with H336.22Spe/I. Thus, when recombinants containing the Kan$^r$ SpeI fragment of H336.22 were selected, they should most often be associated with the SpeI vector fragment of p41KS. We performed transformations with these ligations and obtained Kan$^r$ transformants. The plasmids carried by these transformants were analyzed to identify the recombinants of interest. The desired recombinant plasmid was readily identified among the Kan$^r$ transformants. This recombinant plasmid, termed p41KS22, contains the p41KS-derived insertion in the ketalase gene land the H336.22-derived TnK12 insertion within the acetylase gene. Appropriate restriction digestion analysis confirmed the presence of both insertion mutations and, furthermore, showed that the SpeI fragment containing the TnK12 mutation had been inserted in the correct orientation.

Plasmid p41KS22 was subsequently transferred into a series of *X. campestris* strains via conjugation. The large Gum$^-$ deletion strain X1231 was among the recipients. This deletion lacks all of the gum gene DNA carried on p41KS22; therefore, X1231 carrying p41KS22 should produce non-acetylated, non-pyruvylated xanthan. The plasmid transferred efficiently into X1231, and the resultant phenotype was clearly mucoid but significantly less so than a wild-type control. Polysaccharide produced by X1231 carrying p41KS22 was prepared and analyzed. This polymer contained glucose, mannose, and glucuronic acid but no detectable acetate or pyruvate, demonstrating that X1231 (p41KS22) does produce the expected non-acetylated, non-pyruvylated gum.

Example 15

This example describes the construction and properties of a double mutant plasmid that combines an Acetylase mutation and a Transferase IV mutation.

Capage et al. described methods for isolating and characterizing transposon TnK12 insertions within the cloned gum gene DNA carried by plasmid pRK290-H336. One mutant plasmid carrying such an insertion is pRK290-H336.6. The approximate location of the TnK12 insertion in this plasmid is shown in FIG. 11. When present in the deletion strain X1231, this plasmid directs the synthesis of polytrimer gum as a result of the insertional inactivation of Transderase IV. Using procedures analogous to those described in Example 14, a double mutant plasmid was constructed that combines this Transferase IV defect with the Acetylase mutation carried in pRK290-H336.22. A kanamycin-sensitive derivative of pRK290-H336.6 was derived by deletion of the HindIII fragment of TnK12. This plasmid, p6KS, is analogous to the Kan$^s$ plasmid 41KS and still retains 1 kb of TnK12 inserted within the Transferase IV gene. Subsequently, the large TnK12-containing SpeI fragment of pRK290 H336.22 was ligated into SpeI-digested p6KS plasmid DNA as described in Example 9 and the double mutant plasmid p6KS22 was obtained. This plasmid carries insertion mutations in Transferase IV and the Acetylase. When transferred into deletion strain X1231, it ought to direct the synthesis on non-acetylated polytrimer. However, in several independent plasmid transfer experiments, no transfer of p6KS22 into strain X1231 was detected, although the plasmid was successfully transferred at high frequency into other recipients, including both Gum⁻ and Gum⁺ strains. This result suggests that the presence of p6KS22 in strain X1231 is lethal, probably as a direct result of production of non-acetylated polytrimer gum. Capage et al. described three other lethal mutations within the gum gene cluster and concluded that these lethal mutations cause the accumulation of a toxic intermediate in xanthan biosynthesis. Accumulation of non-acetylated polytrimer could potentially be toxic if this polysaccharide cannot be secreted by the transport system that normally secretes xanthan.

It will be apparent to those skilled in the art that various modifications and variations can be made in the processes and products of the present invention. Thus, it is intended that the present invention cover the modifications and variations of this invention provided they come within the scope of the appended claims and their equivalents.

What is claimed is:

1. A process for preparing a water-soluble polysaccharide polymer comprising repeating pentamer units having a D-glucose:D-mannose:D-glucuronic acid ratio of about 2:2:1, wherein the D-glucose moieties are linked in a beta-[1,4] configuration, inner D-mannose linked in an alpha-[1,3] configuration primarily to alternate glucose moieties, the D-glucuronic acid moieties are linked in a beta-[1,2] configuration to said inner mannose moieties, and outer mannose moieties are linked to said glucuronic acid moieties in a beta-[1,4] configuration, wherein said inner mannose are not acetylated, said process comprising:
   (a) obtaining a mutant *Xanthamonas campestris* which is capable of producing said polysaccharide polymer; and
   (b) culturing said mutant *Xanthomonas campestris* to produce said polysaccharide polymer.

2. The process of claim 1, wherein said outer mannose moieties are not acetylated.

3. The process of claim 1, wherein said outer mannose moieties are not pyruvylated.

4. The process of claim 1, wherein said outer mannose moieties are not acetylated and not pyruvylated.

5. The process of claim 1, wherein at least a portion of said outer mannose moieties are acetylated.

6. The process of claim 5, wherein said outer mannose moieties are not pyruvylated.

7. The process of claim 5, wherein at least a portion of said outer mannose moieties are pyruvylated.

8. The process of claim 1, wherein at least a portion of said outer mannose moieties are pyruvylated.

9. The process of claim 1, further comprising recovering said polysaccharide polymer.

10. The process of claim 1, wherein said mutant *Xanthomonas campestris* is selected from the group consisting of (1) an acetylase I deficient mutant of Xanthomonas campestris, (2) an acetylase I and acetylase II deficient mutant of *Xanthomonas campestris*, (3) an acetylase I and ketalase deficient mutant of *Xanthomonas campestris*, and (4) an acetylase I, acetylase II and ketalase deficient mutant of *Xanthomonas campestris*.

11. The process of claim 10, wherein said mutant *Xanthomonas campestris* is an acetylase I deficient mutant of *Xanthomonas campestris*.

12. The process of claim 10, wherein said mutant *Xanthomonas campestris* is an acetylase I and ketalase deficient mutant of *Xanthomonas campestris*.

13. A process for preparing a water-soluble polysaccharide polymer comprising repeating pentamer units having a D-glucose:D-mannose:D-glucuronic acid ratio of about 2:2:1, wherein the D-glucose moieties are linked in a beta-[1,4] configuration, inner D-mannose linked in an alpha-[1,3] configuration primarily to alternate glucose moieties, the D-glucuronic acid moieties are linked in a beta-[1,2] configuration to said inner mannose moieties, and outer mannose moieties are linked to said glucuronic acid moieties in a beta-[1,4] configuration, wherein said outer mannose moieties are not acetylated and a portion of said inner mannose moieties are acetylated, said process comprising:
   (a) obtaining a mutant *Xanthomonas campestris* which is capable of producing said polysaccharide polymer; and
   (b) culturing said mutant *Xanthomonas campestris* to produce said polysaccharide polymer.

14. The process of claim 13, wherein said outer mannose moieties are not pyruvylated.

15. The process of claim 13, wherein at least a portion of said outer mannose moieties are pyruvylated.

16. The process of claim 13, further comprising recovering said polysaccharide polymer.

17. The process of claim 13, wherein said mutant *Xanthomonas campestris* is selected from the group consisting of (1) an acetylase II deficient mutant of *Xanthomonas campestris*, and (2) an acetylase II and ketalase deficient mutant of *Xanthomonas campestris*.

18. The process of claim 17, wherein said mutant *Xanthomonas campestris* is an acetylase II deficient mutant of *Xanthomonas campestris*.

19. A process for preparing a water-soluble polysaccharide polymer comprising repeating pentamer units having a D-glucose:D-mannose:D-glucuronic acid ratio of about 2:2:1, wherein the D-glucose moieties are linked in a beta-[1,4] configuration, inner D-mannose linked in an alpha-[1,3] configuration primarily to alternate glucose moieties, the D-glucuronic acid moieties are linked in a beta-[1,2] configuration to said inner mannose moieties, and outer mannose moieties are linked to said glucuronic acid moieties in a beta-[1,4] configuration, wherein said outer mannose moieties are not pyruvylated and not acetylated, said process comprising:
   (a) obtaining a mutant *Xanthomonas campestris* which is capable of producing said polysaccharide polymer, and
   (b) culturing said mutant *Xanthomonas campestris* to produce said polysaccharide polymer.

20. The process of claim 19, further comprising recovering said polysaccharide polymer.

21. The process of claim 19, wherein said mutant *Xanthomonas campestris* is an acetylase II and ketalase deficient mutant of *Xanthomonas campestris*.

22. A process for preparing a water-soluble polysaccharide polymer comprising repeating tetramer units having a D-glucose:D-mannose:D-glucuronic acid ratio of about 2:1:1, wherein the D-glucose moieties are linked in a beta-[1,4] configuration, the D-mannose are linked in an alpha-[1,3] configuration primarily to alternate glucose moieties, the D-glucuronic acid moieties are linked in a beta-[1,2] configuration to said mannose moieties, said process comprising:

(a) obtaining a mutant *Xanthomonas campestris* which is capable of producing said polysaccharide polymer; and
   (b) culturing said mutant *Xanthomonas campestris* to produce said polysaccharide polymer.

23. The process of claim 22, wherein at least a portion of said mannose moieties are acetylated.

24. The process of claim 22, wherein said mannose moieties are not acetylated.

25. The process of claim 22, further comprising recovering said polysaccharide polymer.

26. The process of claim 22, wherein said mutant *Xanthomonas campestris* is selected from the group consisting of (1) a transferase V deficient mutant of *Xanthomonas campestris*, (2) a transferase V and acetylase I deficient mutant of *Xanthomonas campestris*, and (3) a transferase V and acetyl coenzyme A deficient mutant of *Xanthomonas campestris*.

27. The process of claim 26, wherein said *Xanthomonas campestris* is a transferase deficient mutant of *Xanthomonas campestris*.

28. A mutant *Xanthomonas campestris* capable of producing a water-soluble polysaccharide polymer comprising repeating pentamer units having a D-glucose:D-mannose:D-glucuronic acid ratio of about 2:2:1, wherein the D-glucose moieties are linked in a beta-[1,4] configuration, inner D-mannose linked in an alpha-[1,3] configuration primarily to alternate glucose moieties, the D-glucuronic acid moieties are linked in a beta-[1,2] configuration to said inner mannose moieties, and outer mannose moieties are linked to said glucuronic acid moieties in a beta-[1,4] configuration, wherein said inner mannose moieties are not acetylated, wherein said mutant *Xanthamonas campestris* is selected from the group consisting of (1) an acetylase I deficient mutant of *Xanthomonas campestris*, (2) an acetylase I and acetylase II deficient mutant of *Xanthomonas campestris*, (3) an acetylase I and ketalase deficient mutant of *Xanthomonas campestris*, and (4) an acetylase I, acetylase II and ketalase deficient mutant of *Xanthomonas campestris*.

29. A mutant *Xanthomonas campestris* capable of producing a water-soluble polysaccharide polymer comprising repeating pentamer units having a D-glucose:D-mannose:D-glucuronic acid ratio of about 2:2:1, wherein the D-glucose moieties are linked in a beta-[1,4] configuration, inner D-mannose linked in an alpha-[1,3] configuration primarily to alternate glucose moieties, the D-glucuronic acid moieties are linked in a beta-[1,2] configuration to said inner mannose moieties, and outer mannose moieties are linked to said glucuronic acid moieties in a beta-[1,4] configuration, wherein said outer mannose moieties are not acetylated and a portion of said inner mannose moieties are acetylated, wherein said mutant *Xanthomonas campestris* is selected from the group consisting of (1) an acetylase II deficient mutant of *Xanthomonas campestris*, and (2) an acetylase II and ketalase deficient mutant of *Xanthomonas campestris*.

30. A mutant *Xanthomonas campestris* capable of producing a water-soluble polysaccharide polymer comprising repeating tetramer units having a D-glucose:D-mannose:D-glucuronic acid ratio of about 2:1:1, wherein the D-glucose moieties are linked in a beta-[1,4] configuration, the D-mannose are linked in an alpha-[1,3] configuration primarily to alternate glucose moieties, the D-glucuronic acid moieties are linked in a beta-[1,2] configuration to said mannose moieties, wherein said mutant *Xanthomonas campestris* is selected from the group consisting of (1) a transferase V deficient mutant of *Xanthomonas campestris*, (2) a transferase V and acetylase I deficient mutant of *Xanthomonas campestris*, and (3) a transferase V and acetyl coenzyme A deficient mutant of *Xanthomonas campestris*.

31. *Xanthomonas campestris* strain X1397, having accession number 68033.

32. *Xanthomonas campestris* strain X1398, having accession number 68034.

33. *Xanthomonas campestris* strain X1399, having accession number 68035.

34. *Xanthomonas campestris* strain X1400, having accession number 68036.

35. *Xanthomonas campestris* strain X1401, having accession number 68037.

36. *Xanthomonas campestris* strain X1402, having accession number 68038.

37. *Xanthomonas campestris* strain X1403, having accession number 68039.

38. *Xanthomonas campestris* strain X1006, having accession number 53473.

39. *Xanthomonas campestris* strain X921, having accession number 53472.

40. *Xanthomonas campestris* strain X934, having accession number 53474.

41. *Xanthomonas campestris* strain X1231, having accession number 67344.

42. *Xanthomonas campestris* strain X1910, having accession number 202034.

\* \* \* \* \*